(12) United States Patent
Slobodkin et al.

(10) Patent No.: US 8,057,821 B2
(45) Date of Patent: Nov. 15, 2011

(54) BIODEGRADABLE CROSS-LINKED CATIONIC MULTI-BLOCK COPOLYMERS FOR GENE DELIVERY AND METHODS OF MAKING THEREOF

(75) Inventors: Gregory Slobodkin, Huntsville, AL (US); Majed Matar, Madison, AL (US); Jason Fewell, Madison, AL (US); Khursheed Anwer, Madison, AL (US)

(73) Assignee: EGEN, Inc., Huntsville, AL (US)

( * ) Notice: Subject to any disclaimer, the term of this patent is extended or adjusted under 35 U.S.C. 154(b) by 1386 days.

(21) Appl. No.: 10/981,135

(22) Filed: Nov. 3, 2004

(65) Prior Publication Data

US 2006/0093674 A1    May 4, 2006

(51) Int. Cl.
 *A61K 48/00*    (2006.01)
(52) U.S. Cl. .................. 424/486; 528/310; 528/332
(58) Field of Classification Search .............. 528/310, 528/332; 424/486
 See application file for complete search history.

(56) References Cited

U.S. PATENT DOCUMENTS

| | | | |
|---|---|---|---|
| 4,476,266 A * | 10/1984 | Maeda et al. | 524/128 |
| 5,733,462 A * | 3/1998 | Mallon et al. | 210/728 |
| 6,333,051 B1 | 12/2001 | Kabano et al. | |
| 6,359,054 B1 | 3/2002 | Lemieux et al. | |
| 6,521,340 B2 * | 2/2003 | Rainer | 428/402 |
| 6,652,886 B2 | 11/2003 | Ahn et al. | |
| 6,696,038 B1 * | 2/2004 | Mahato et al. | 424/1.45 |
| 6,890,556 B1 * | 5/2005 | Segura et al. | 424/450 |
| 2003/0073619 A1 | 4/2003 | Mahato et al. | |
| 2003/0166601 A1* | 9/2003 | Woodle et al. | 514/44 |

FOREIGN PATENT DOCUMENTS

WO    WO 03/046185    6/2003

OTHER PUBLICATIONS

Ahn, Cheol-Hee et al., Biodegradable poly(ethylenimine) for plasmid DNA delivery, J. Controlled Release, vol. 80, 2002, pp. 273-282.
Feast, J.W. et al., Synthesis, Structure and Properties of some Hyperbranched Polyesters, J. Mater. Chem., vol. 5, 1995, pp. 405-411.
Forrest, M.L. et al., A Degradable Polyethylenimine Derivative with Low Toxicity for Highly Efficient Gene Delivery, Bioconjugate Chem., vol. 14, 2003, pp. 934-940.
Gosselin, M.A. et al., Efficient Gene Transfer Using Reversibly Cross-Linked Low Molecular Weight Polyethylenimine, Bioconjugate Chem. vol. 12, 2001, pp. 989-994.
Lee, Minhyung et al., Prevention of autoimmune insulitis by delivery of a chimeric plasmid encoding interleukin-4 and interleukin-10, J. Controlled Rel., vol. 88, 2003, pp. 333-342.
Lim, Yong-Beom et al. Biodegradable Polyester, Poly [α-(4-Aminobutyl)-L-Glycolic Acid], as a Non-Toxic Gene Carrier, Pharmaceutical Res., vol. 17, No. 7, 2000, pp. 811-816.
Lim, Yong-beom et al., A Self-Destroying Polycationic Polymer: Biodegradable Poly(4-hydroxy-L-proline ester), J. Am. Chem. Soc. vol. 121, 1999, pp. 5633-5639.
Lim, Young-beom et al., Biodegradable, Endosome Disruptive, and Cationic Network-type Polymer as a Highly Efficient and Nontoxic Gene Delivery Carrrier, Bioconjugate Chem., vol. 13, 2002, pp. 952-957.
Maheshwari, A., et al., Biodegradable polymer-based interleukin-12 gene delivery: role of induced cytokines, tumor infiltrating cells and nitric oxide in anti-tumor activity, Gene Ther., vol. 9, 2002, pp. 1075-1084.
Putnam, D., Poly(4-hydroxy-L-proline ester): Low-Temperature Polycondensation and Plasmid DNA Complexation, Macromolecules, vol. 32, 1999, pp. 3658-3662.
Sperling, L.H. Intro to Physical Polymer Science, 3$^{rd}$ Ed. Wiley 2001, pp. 96-102.
Tanaka, R. et al., High Molecular Weight Linear Poly(ethylenimine) and Poly(N-methylethylenimine) Macromolecules vol. 16, 1983 pp. 849-853.
Thomas, Mini et al., Enhancing polyethylenimine's delivery of plasmid DNA into mammalian cells, Proc. Nat. Acad. Sci., vol. 99 (23), 2002, pp. 14640-14645.

* cited by examiner

*Primary Examiner* — James J Seidleck
*Assistant Examiner* — Gregory Listvoyb
(74) *Attorney, Agent, or Firm* — McDonnell Boehnen Hulbert & Berghoff LLP

(57) ABSTRACT

A biodegradable cross-linked cationic multi-block copolymer of linear polyethylenimine (LPEI) wherein the LPEI blocks are linked together by hydrophilic linkers with a biodegradable disulfide bond and methods of making thereof. The biodegradable cross-linked cationic multi-block copolymer may also contain pendant functional moieties which are preferably receptor ligands, membrane permeating agents, endosomolytic agents, nuclear localization sequences, pH sensitive endosomolytic peptides, chromogenic or fluorescent dyes.

15 Claims, 13 Drawing Sheets

BIODEGRADABLE CROSS-LINKED CATIONIC MULTI-BLOCK COPOLYMERS FOR GENE DELIVERY AND METHODS OF MAKING THEREOF

FIELD OF THE INVENTION

This invention relates generally to biodegradable cross-linked cationic multi-block copolymers and methods of preparing thereof. It relates particularly to the composition of and a method for preparation of biodegradable cross-linked cationic multi-block copolymers comprising a low molecular weight linear polyethylenimine (LPEI) and a biodegradable linker, wherein every LPEI unit is covalently bound to the next unit(s) via the biodegradable linker. It also relates to the composition of and a method for preparation of fluorescent labeled polymers comprising the aforementioned biodegradable cross-linked cationic multi-block copolymers and a fluorescent tag. The biodegradable cross-linked cationic multi-block copolymers of the present invention are useful for the delivery of DNA, RNA, oligonucleotides, and other anionic agents by facilitating their transmembrane transport or by enhancing their adhesion to biological surfaces, and cellular localization thereof.

BACKGROUND OF THE INVENTION

The success of gene therapy relies on the ability of gene delivery systems to efficiently and safely deliver the therapeutic gene to the target tissue. Gene delivery systems can be divided into viral and non-viral (or plasmid DNA-based). The present gene delivery technology being used in clinics today can be considered first generation, in that they possess the ability to transfect or infect target cells through their inherent chemical, biochemical, and molecular biological properties. Relying on these sole properties, however, limits therapeutic applications. For example, viruses with the ability to infect mammalian cell, have been effectively used for gene transfer with high transduction efficiency. However, serious safety concerns (e.g., strong immune response by the host and potential for mutagenesis) have been raised when used in clinical applications.

The non-viral gene delivery systems, based on "naked DNA" or formulated plasmid DNA, have potential benefits over viral vectors due to simplicity of use and lack of inciting a specific immune response. A number of synthetic gene delivery systems have been described to overcome the limitations of naked DNA, including cationic lipids, peptides, and polymers. Despite early optimism, the clinical relevance of the cationic lipid-based systems is limited due to their low efficiency, toxicity, and refractory nature.

Polymers, on the other hand, have emerged as a viable alternative to current systems because their excellent molecular flexibility allows for complex modifications and incorporation of novel chemistries. Cationic polymers, such as poly (L-lysine) (PLL) and poly(L-arginine) (PLA), polyethyleneimine (PEI) have been widely studied as gene delivery candidates due to their ability to condense DNA, and promote DNA stability and transmembrane delivery. The transfection efficiency of the cationic polymers is influenced by their molecular weight. Polymers of high molecular weight, >20 kD, have better transfection efficiency than polymers of lower molecular weight. Ironically, those with high molecular weights are also more cytotoxic. Several attempts have been made to circumvent this problem and improve the transfection activity of cationic polymers without increasing their cytotoxicity. For example, Lim et al. have synthesized a degradable polymer, poly [α-(4-aminobutyl)-L-glycolic acid] (PAGA) by melting condensation. *Pharm. Res.* 17:811-816, 2000. Although PAGA has been used in some gene delivery studies, its practical application is limited due to low transfection activity and poor stability in aqueous solutions. *J Controlled. Rel.* 88:33-342, 2003; *Gene Ther.* 9:1075-1084, 2002 Hydroxyproline ester (PHP ester) and networked poly (amino ester) are among a few other examples of degradable polymers. The PHP ester has been synthesized from Cbz-4-hydroxy-L-proline by melting condensation or by dicyclohexylcarbodiimide (dimethyl-amino)pyridine (DCC/DMAP)-activated polycondensation. *J. Am. Chem. Soc.* 121: 5633-5639, 1999; *Macromolecules* 32:3658-3662, 1999 The networked poly(amino ester) (n-PAE) has been synthesized using bulk polycondensation between hydroxyl groups and carboxyl groups of bis(2-methoxy-carbonylethyl)[tris-(hydroxymethyl)methyl]amine followed by condensation with 6-(Fmoc-amino)hexanoic acid (Bioconjugate Chem. 13:952-957, 2002). These polyesters have been shown to condense DNA and transfect cells in vitro with low cytotoxicity, but their stability in aqueous solutions is poor.

Poly(ethyleneimine) (PEI) efficiently condenses DNA into small narrowly distributed positively charged spherical complexes and can transfect cells in vitro and in vivo. PEI is similar to other cationic polymers in that the transfection activity of PEI increases with increasing polymer/DNA ratios. A distinct advantage of PEI over PLL is its endosomolytic activity which enables PEI to yield high transfection efficiency. Commercial branched PEI is composed of 25% primary amines, 50% secondary amines and 25% tertiary amines. The overall protonation level of PEI doubles from pH 7 to pH 5, which means in the endosome PEI becomes heavily protonated. Protonation of PEI triggers chloride influx across the endosomal membrane, and water follows to counter the high ion concentration inside the endosome, which eventually leads to endosomal disruption from osmotic swelling and release of the entrapped DNA. Because of its intrinsic endosomolytic activity, PEI generally does not require the addition of an endosomolytic agent for transfection. Due to these advantages PEI has been increasingly utilized in polymer functionalization strategies to create safer and more efficient delivery systems. The cytotoxicity and transfection activity of PEI is linearly related to the molecular weight of the polymer. To increase PEI transfection activity without raising its cytotoxicity, Ahn et al. has synthesized a high molecular weight multi-block copolymer by covalently linking small molecular weight branched PEI blocks to PEG molecules via amide linkages. *J Control Release* 80:273-282, 2002; U.S. Pat. No. 6,652,886 These multi-block co-polymers are poorly soluble in aqueous solutions and are only modestly better than the single block polymers in transfection activity (at best 3-fold higher).

BRIEF SUMMARY OF THE INVENTION

The present invention provides a biodegradable cross-linked cationic multi-block copolymer of linear poly(alkylenimine) (LPAI) and a hydrophilic linker, wherein said LPAI blocks are crossed linked together by said hydrophilic linker with biodegradable ester, amide, disulfide, or phosphate linkages bonds. Preferably, the linear poly(alkylenimine) (LPAI) is a member selected from the group consisting of polyethyleneimine, polypropylenimine, aminoglycoside-polyamine, dideoxy-diamino-β-cyclodextrin, spermine and spermidine. More preferably, the linear poly(alkylenimine) (LPAI) is linear poly(ethyleneimine) (LPEI).

The cross-linked cationic multi-block copolymer of the present invention can be optionally linked by the biodegradable linkers to other moieties such as, for example, fluorescent markers, lipids anchors or their derivatives, i.e., cholesterol, fatty acids or their derivatives. Preferably, the molecular weight of the linear PEI used in this invention is within the range of 1000 to 25000 Daltons. The linear PEI blocks are preferably linked to one another via a diamide linkage utilizing a biodegradable disulfidediacid-derived linker, i.e., dithiodipropionate derivatives. The molar ratio of the linker to the PEI is preferably within a range of 1/1 to 5/1; the molar ratio of the lipid anchors to PEI is preferably from 0/1 to 3/1. The polymer of the present invention is formulated as a polyammonium salt, preferably with a chloride counterion. Since the toxicity of PEI increases with an increase in its molecular weight, the use of lower molecular weight PEIs as blocks in the polymer of the present invention provides an improved gene carrier for use as a general reagent for transfection of mammalian cells, and for the in vivo application of gene therapy.

The biodegradable, cross-linked cationic multi-block copolymer of this invention can spontaneously form discrete nanometer-sized particles with a nucleic acid, which promotes gene transfection into mammalian cell lines more efficiently than can be achieved conventionally with Lipofectamine™ and simple polyethyleneimines. The biodegradable, cross-linked cationic multi-block copolymer of the present invention is readily susceptible to metabolic degradation after incorporation into animal cells. Moreover, the biodegradable, cross-linked cationic multi-block copolymer of the present invention can form an aqueous micellar solution which is particularly useful for systemic delivery of various bioactive agents such as DNA.

The present invention further provides transfection formulations, comprising a biodegradable, cross-linked cationic multi-block copolymer, complexed with a selected nucleic acid in the proper charge ratio (positive charge of the lipopolymer/negative charge of the nucleic acid) that is optimally effective both for in vivo and in vitro transfection. The present invention also provides a transfection reagent that can be visualized by fluorescence microscopy due to its covalently linked fluorophore (for example, a rhodamine) thus providing a tool to visualize cell distribution and trafficking of the polymer and its complexes with anionic agents.

The present invention also provides a synthesis procedure for the synthesis of a linear polyethyleneimine (PEI) in a sulfate form. The present invention also provides preparation procedures for biodegradable and water soluble, cross-linked cationic multi-block copolymer capable of condensing nucleic acids or other anionic bioactive agents and forming stable complexes under physiological conditions. The present invention also provides preparation procedures for biodegradable and water soluble multi-block polymers carrying specialized tracers, i.e., fluorescent markers or some other functionalized ligands. Such polymers are capable of condensing nucleic acids or other anionic bioactive agents and forming stable complexes under physiological conditions, with additional advantages for use in analytical and research work.

DETAILED DESCRIPTION

Figure 1:
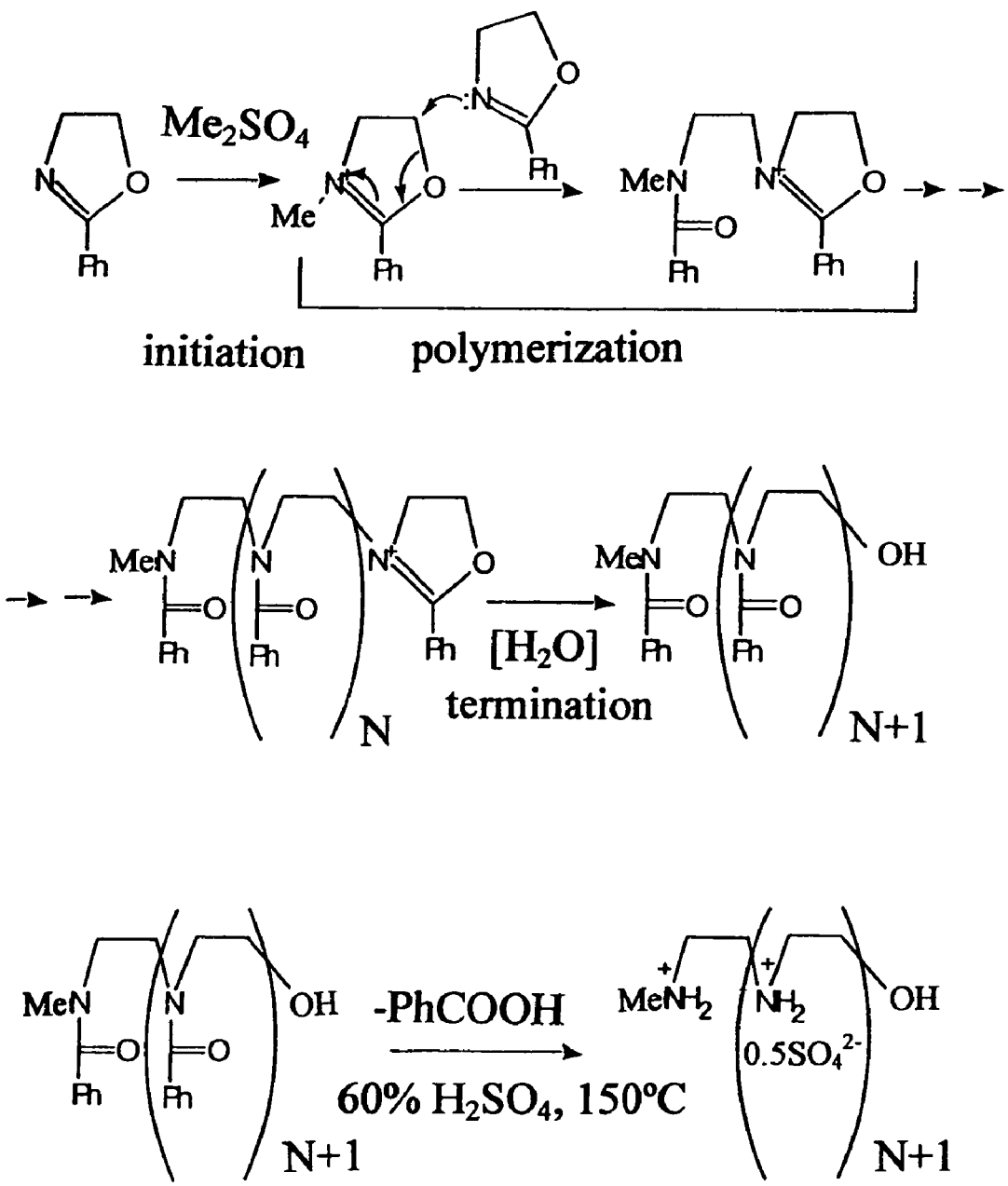
FIG. 1 illustrates the synthesis scheme of the linear PEI (LPEI) of the present invention.

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a disulfide link" includes reference to two or more of such disulfide links, reference to "a ligand" includes reference to one or more of such ligands, and reference to "a drug" includes reference to two or more of such drugs.

In describing and claiming the present invention, the following terminology will be used in accordance with the definitions set out below.

"Transfecting" or "transfection" shall mean transport of nucleic acids from the environment external to a cell to the internal cellular environment, with particular reference to the cytoplasm and/or cell nucleus. Without being bound by any particular theory, it is to be understood that nucleic acids may be delivered to cells either after being encapsulated within or adhering to one or more cationic polymer/nucleic acid complexes or being entrained therewith. Particular transfecting instances deliver a nucleic acid to a cell nucleus. Nucleic acids include DNA and RNA as well as synthetic congeners thereof. Such nucleic acids include missense, antisense, nonsense, as well as protein producing nucleotides, on and off and rate regulatory nucleotides that control protein, peptide, and nucleic acid production. In particular, but not limited to, they can be genomic DNA, cDNA, mRNA, tRNA, rRNA, hybrid sequences or synthetic or semi-synthetic sequences, and of natural or artificial origin. In addition, the nucleic acid can be variable in size, ranging from oligonucleotides to chromosomes. These nucleic acids may be of human, animal, vegetable, bacterial, viral, or synthetic origin. They may be obtained by any technique known to a person skilled in the art. As used herein, the term "bioactive agent" or "drug" or any other similar term means any chemical or biological material or compound suitable for administration by the methods previously known in the art and/or by the methods taught in the present invention, which induce a desired biological or pharmacological effect, which may include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anesthetic effect, or it may be systemic.

This invention is not drawn to novel drugs or to new classes of bioactive agents per se. Rather it is drawn to biodegradable cationic copolymer compositions and methods of using such compositions for the delivery of genes or other bioactive agents that exist in the state of the art or that may later be established as active agents and that are suitable for delivery by the present invention. Such substances include broad classes of compounds normally delivered into the body. In general, this includes but is not limited to: nucleic acids, such as DNA, RNA, and oligonucleotides, anti-infective such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium, calcium channel blockers, beta-blockers, alpha-blockers, and antiarrhythmics; antihypertensives; diuretics and antidiuretics; vasodilators including general, coronary, peripheral and cerebral; central nervous system stimulants; vasoconstrictors; cough and cold preparations, including decongestants; hormones such as estradiol and other steroids including corticosteroids; hypnotics; immunosuppressives; muscle relaxants; parasympatholytics; psychostimulants; sedatives; and tranquilizers. By the method of the present invention, drugs in all forms, e.g. ionized, nonionized, free base, acid addition salt, and the like may be delivered, as can drugs of either high or low molecular weight. The only limitation to the genus or species of bioactive agent to be delivered is that of functionality which can be readily determined by routine experimentation.

As used herein, the term "biodegradable" or "biodegradation" is defined as the conversion of materials into less complex intermediates or end products by solubilization hydrolysis, or by the action of biologically formed entities which can be enzymes and other products of the organism.

As used herein, "effective amount" means the amount of a nucleic acid or a bioactive agent that is sufficient to provide the desired local or systemic effect and performance at a reasonable risk/benefit ratio as would attend any medical treatment.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate; and the like.

As used herein, "administering" and similar terms mean delivering the composition to the individual being treated such that the composition is capable of being circulated systemically where the composition binds to a target cell and is taken up by endocytosis. Thus, the composition is preferably administered to the individual systemically, typically by subcutaneous, intramuscular, transdermal, intravenous, or intraperitoneal routes. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like.

Fundamental to the success of gene therapy is the development of gene delivery vehicles that are safe and efficacious after systemic administration. The present invention provides for an efficient non-viral polymer-based gene carrier for delivery of nucleic acids to a target cell. One embodiment of the present invention relates to biodegradable, cross-linked cationic multi-block copolymers comprising low molecular weight linear PEI blocks and a dithioacid moiety, i.e., dithiodipropionic acid, as biodegradable linkers. The biodegradable, cross-linked cationic multi-block copolymers of the present invention are synthesized by cross-linking low molecular weight linear PEI units via a biodegradable disulfide linkage. These biodegradable cross-linked cationic multi-block copolymers are water soluble and transfectionally superior (68-70 fold higher activity) to single block polymers. This vast difference in transfection activity between the copolymers of the present invention and that of current available polymers may be due to the differences in the polymer composition, synthesis scheme and physiochemical properties.

For example, the multi-block copolymers of the present invention are synthesized using linear polyethyleneimine (LPEI) blocks, which exhibit rather distinct solubility patterns as compared to branched polyethyleneimines. Since the structure of linear PEIs does not possess any primary amines, different linking/coupling reagents are used in the present invention compared to those used in previous reports. *Bioconjugate Chem.,* 2003, 14, 934; *Bioconjugate chem.* 2001, 12, 989 Furthermore, when molecular weight ratio of the linker to the branched PEI is ≧1, it may cause significant dilution of the polyamine backbone of the cationic polymer and may have been the reason for the modest increase in the transfection activity of their cross-linked product. In the present invention, short linkers are used and the linker to the polymer molecular weight ratio is <0.2 which minimizes the dilution of polyamine polymer backbone. Another significant difference between the present invention and the prior art is the nature of the chemical bond between the linker and the polymer blocks. Preferably, the present invention uses disulfide bonds which can be biodegraded more easily as compared to amide bonds. Other biodegradable bonds can also be used in the present invention includes: phosphoesters, hydrazone, cis-asotinyl, urethane and poly(ethyl). Since any linker reacts in stepwise fashion, it can link either different blocks or the different areas of the same block (loop formation). The latter will favor the formation of a lightly cross-linked material with poor solubility due to multiple looping. The process of the present invention solve this problem by incorporating partial and reversible blocking/protection of nitrogen atoms in the LPEI blocks. Such LPEI functionalization also increases polymer solubility, facilitating the linking of LPEI blocks. This process also allows for convenient incorporation of pendant auxiliary ligands (for example, lipids, or fluorescent markers) onto a cationic polymer. Finally, the biodegradable, cross-linked, cationic, multi-block copolymer of the present invention is water soluble and expresses high transfection activity (68-70 fold increase in transfection activity over single block polymers), while the multi-block copolymers of the prior art are poorly water soluble and only modestly better in activity (3-4 fold) over the single block polymers.

In general, the cationic block copolymers of the present invention can be represented by the following formula:

wherein CP represents a cationic polymer containing at least one secondary amine group, said CP polymer has a number averaged molecular weight within the range of 1000 Daltons to 25000 Daltons; Y represents a bifunctional biodegradable linker containing ester, amide, disulfide, or phosphate linkages; L represents a ligand; x is an integer in the range from 1 to 20; y is an integer from 1 to 100; and z is an integer in the range from 0 to 40.

More specifically, preferred embodiments of the present invention can be represented by the following formula:

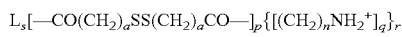

wherein $(CH_2)_n$ is an aliphatic carbon chain which covalently attaches to nitrogens and forms the backbone of a linear polyalkyleneimine block; L represents a ligand selected from the group consisting of lipids, fluorescent markers and targeting moieties; $[—CO(CH_2)_aSS(CH_2)_aCO—]$ represents a biodegradable dithiodiacid linker; wherein range of integer a is an integer from 1 to 15; n is an integer from 2 to 15; p is an integer from 1 to 100; q is an integer from 20-500; r is an integer from 1 to 20; and s is an integer from 1 to 40.

Figure 2:
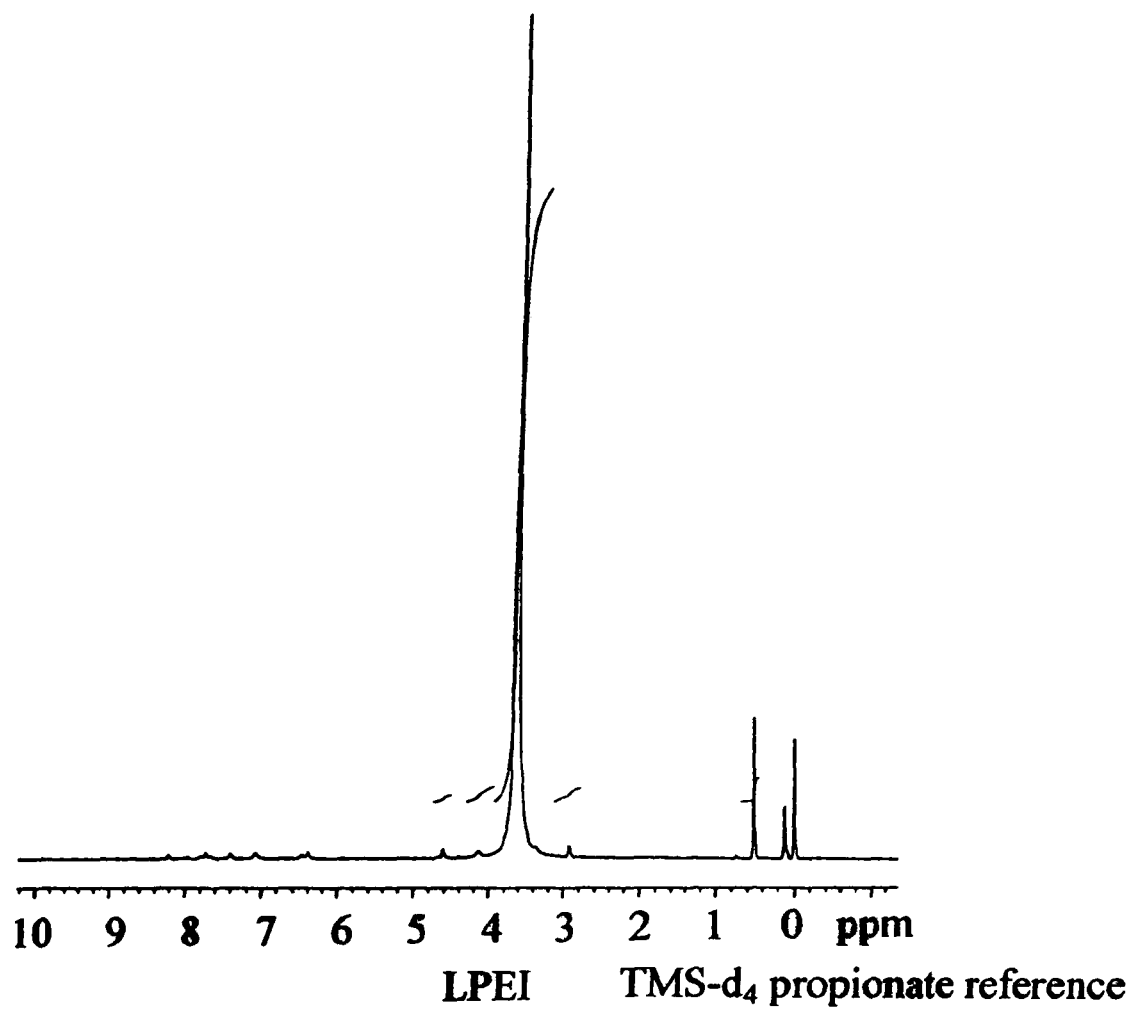
FIG. 2 shows 1H NMR data for analysis of the LPEI.

The linear polyethyleneimine of various molecular weights can be synthesized as illustrated in FIG. 1, which is slightly modified based on Tanaka's procedure. *Macromolecules,* 16: 849-853, 1983. Specifically, purified 2-phenyl-2-oxazoline is polymerized in bulk at 140° C. in the presence of varying amounts of initiator $Me_2SO_4$. The poly(N-benzoyl ethyleneimine)s obtained are hydrolyzed by heating to 140-150° C. with 60% $H_2SO_4$. After removal of the byproduct benzoic acid by steam distillation, LPEIs (NMR is depicted in FIG. 2) are separated in high yield on cooling in the form of sulfate salts (stoichiometry close to sulfate hydrate, with one sulfate and one molecule of water per each two nitrogens). The preservation of backbone integrity during harsh hydrolysis conditions was indicated by the measurement of the molecular weights of re-benzoylated LPEI-free bases (vide infra).

These sulfate salts of the LPEIs possess low solubility under normal conditions, but are soluble either in strong acids (pH<0) or in mild aqueous bases (like $NaHCO_3$—deprotonation of polyammonium polymer backbone and disruption of LPEI sulfate crystalline lattice). This low solubility of sulfate salts of LPEIs and their derivatives has been advantageously used by us in isolation and purification of LPEIs and their derivatives. Other, more soluble salts of LPEIs could be prepared from the sulfates by exchange with corresponding barium salts. Free bases (as poorly soluble hydrates) are prepared by treating the sulfates with a large excess of NaOH. A series of LPEIs with Mws from 2 kD to 20 kD can be prepared in this way.

Figure 3:
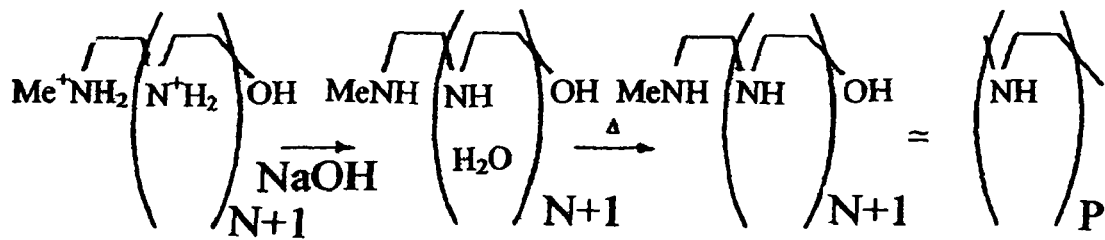
FIG. 3 illustrates the synthesis scheme of biodegradable, cross-linked, cationic multi-block copolymers of LPEI of the present invention.
Figure 3:
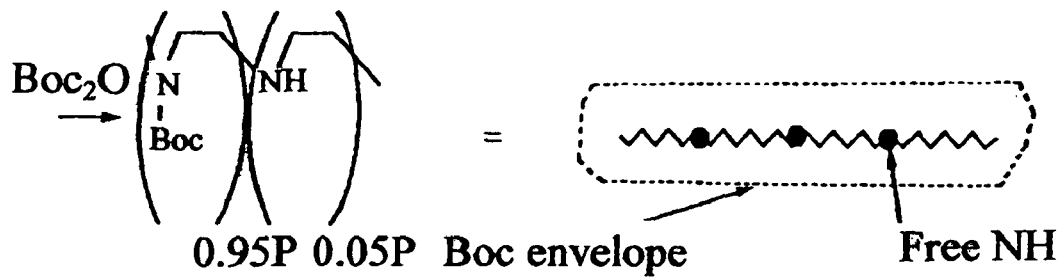
Figure 3:
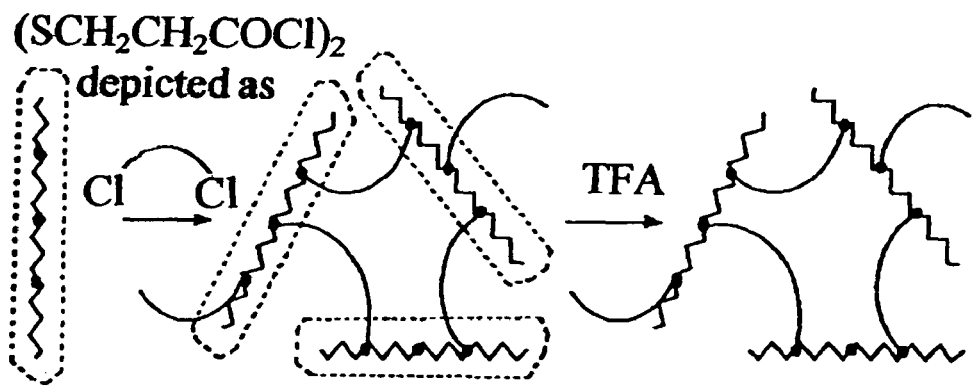
Figure 3:
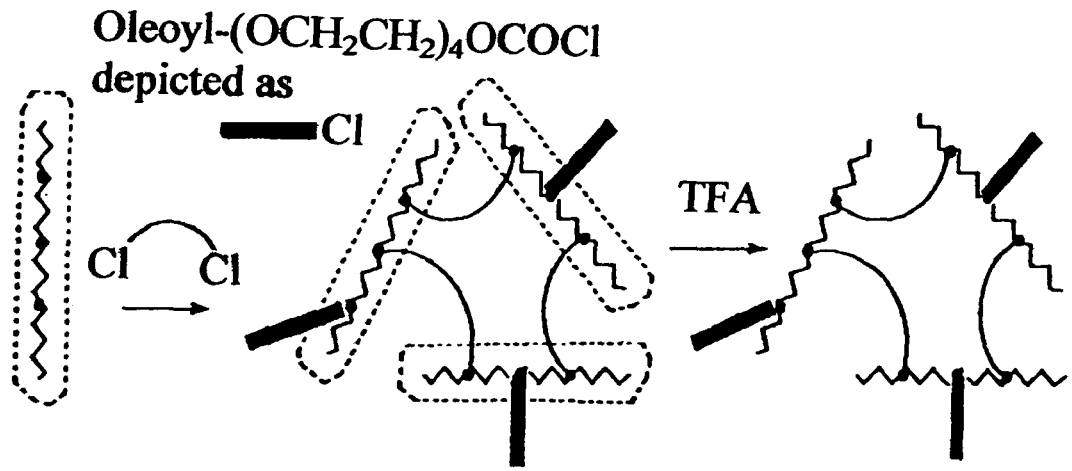

The biodegradable cross-linked cationic multi-block copolymers of LPEI can be synthesized as illustrated in FIG. 3. Chemical modification of LPEIs presents certain inconveniences due to their low solubility as hydrates and hygroscopicity as anhydrous free bases. Any bifunctional linker used for PEI cross-linking can form a link either between two nitrogen atoms belonging to the same polymer block (i.e. forming a loop without actually linking polymer molecules) or between two nitrogen atoms from different polymer blocks (i.e. truly linking polymer blocks). Since it is very difficult to distinguish between these two modes of linkage spectroscopically, the easiest analytical tests would be determination of molecular weight by light scattering or solution viscosity measurements and determination of the biological activity of the resulting multiblock product. *J. Mater. Chem.* 1995, 5, 405-411 In the vicinity of any given nitrogen atom the [local] concentration of the same-backbone nitrogens is high and not dependent on the solution concentration, while the concentration of the nitrogens from the different backbones is low and concentration dependent. Therefore, under normal conditions, loop formation can be expected to be the preferred reaction pathway for the linker.

In order to minimize such loop formation, one could use (at least one) of the following approaches. The first approach is by increasing the concentration of the polymer molecules in the reaction mixture. However, polymer solubility poses obvious limitations on this approach. The second approach is by decreasing the number of available nitrogen atoms on every polymer molecule by reversible blocking with a suitable protecting group. This also increases the solubility of LPEIs in organic solvents. At the limit, with only one nitrogen atom available per molecule, loop formation becomes impossible and the only possible aggregate is a dimer. For less exhaustively protected polymers, the local concentration of nitrogen atoms from other polymer chains declines in parallel with that of the same-chain nitrogens but can be made comparable to it, leading to a 50% chance of linking vs. loop formation.

If its attachment is visualized as occurring stepwise, one could get within its reach not only the proximate area of the already attached polymer molecule, but also a much greater volume of the solution. If the polymer concentration is sufficiently high so that another polymer molecule comes within this volume and becomes available (together with the remainder of the already attached polymer molecule), the probability of polymer blocks linking increases. The obvious drawback of this approach is the necessity of using very long linkers with correspondingly high molecular weights and unavoidable dilution of the cross-linked product with high mass linkers.

Figure 4:
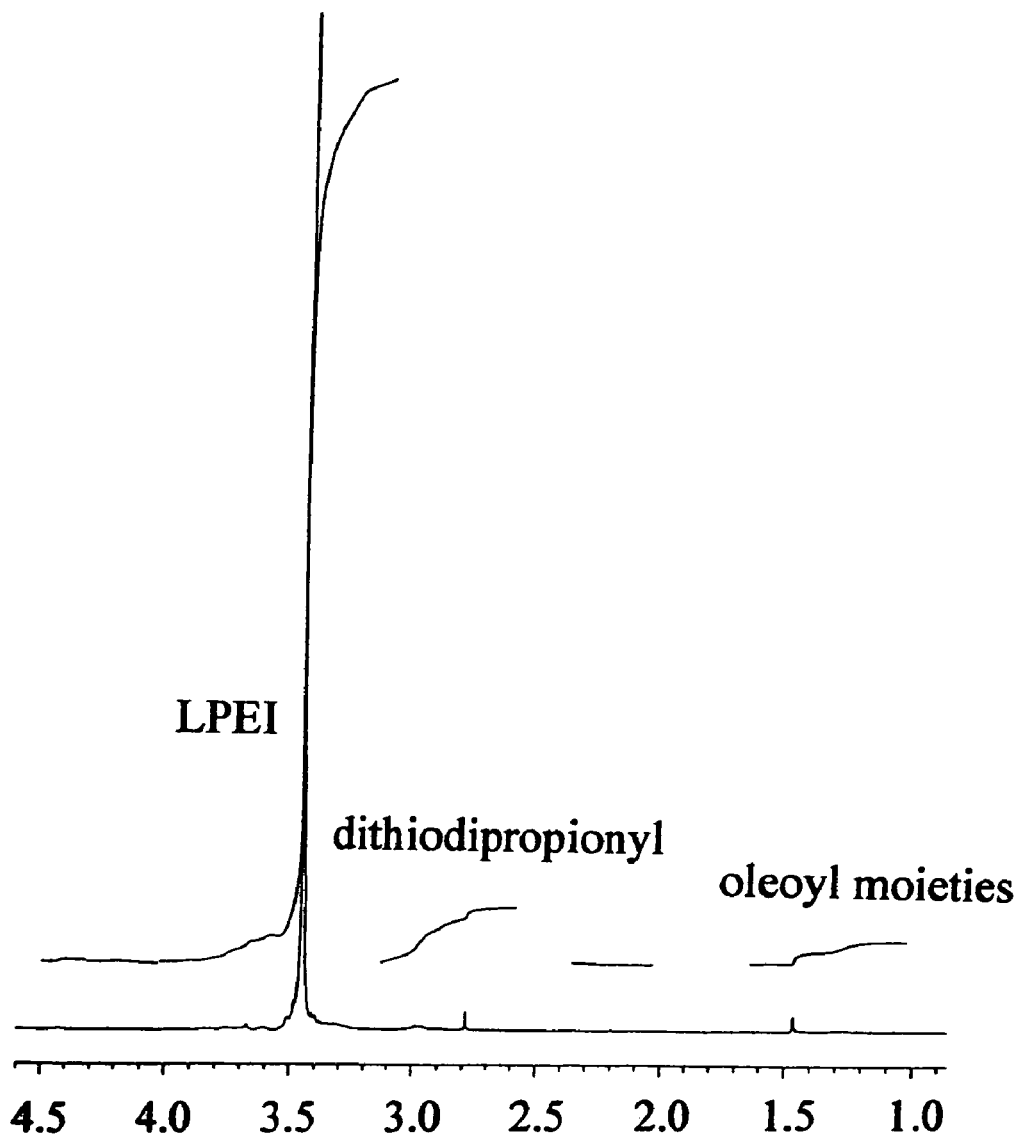
FIG. 4 shows 1H NMR data for analysis of biodegradable, cross-linked, cationic multi-block lipopolymers of LPEI 3.6K (BD3.6K-O) with a lipid moiety.

Based on these considerations the use of higher PEI aggregates is problematic. Therefore, in the present invention, a linear PEI with lowest (less-toxic) molecular weight is chosen as the PEI building block. Macromolecules, 1983, vol 16, 849; J. Polym. Sci. Polym. Lett. Ed. 1978, vol 16 (1), 13 Having investigated LPEIs of different molecular weights for gene transfection capacity and toxicity, LPEI with an MW of 3.6K is chosen as suitable LPEI blocks. A tert-butoxycarbonyl (Boc) group is used as a removable protecting group. The anhydrous LPEIs are then converted into their non-exhaustively protected forms. It is found that 90%-95% Boc incorporation produces optimal results. The materials obtained possess greater solubility and are amenable to chemical modification on their remaining free NH groups. The NMR of these polymers is depicted in FIG. 4. This approach is preferable for linking several smaller LPEI molecules due to minimization of loop formation which is unavoidable when using unprotected LPEI.

Using biodegradable (for example, disulfide) linkers, it makes sense to connect LPEIs of smaller size which should minimize the toxicities associated with using LEPIs. A conceptually similar approach—physical aggregation of hydrophobically modified branched PEIs of low molecular weight—was used by Klibanov et al. and branched PEIs have been linked before. Proc. Nat. Acad. Sci., 2002, vol. 99(23) 14640; U.S. Pat. No. 6,652,886; Bioconjugate Chem., 2003, 14, 934; Bioconjugate chem. 2001, 12, 989 However, these authors use disulfide linking reagents specific to the primary amino groups of BPEIs and non-preparative laborious purification by gel-permeation chromatography. The procedures of the present invention do not have these limitations. It is found that it is convenient to attach pendant ligands to the polyethyleneimine blocks in a one-pot reaction at the same time as the block linking is accomplished. Another advantage of the synthetic scheme of the present invention is the use of LPEIs which are more active than their branched isomers.

The biodegradable, cross-linked, cationic, multi-block copolymers of LPEI and lipopolymers of the present invention have amine groups that are electrostatically attracted to polyanionic compounds such as nucleic acids. The cationic copolymer of the present invention condenses DNA and forms compact structures. In addition, low toxicity of monomeric degradation products after delivery of bioactive materials provides for gene carriers with reduced cytotoxicity and increased transfection efficiency.

The biodegradable cross-linked cationic multi-block copolymers of the present invention can also be conjugated with tracers (for example, fluorescent markers) or targeting ligands either directly or via spacer molecules. Preferably, only a small portion of the available amino groups is coupled to the ligand. The targeting ligands conjugated to the polymers direct the polymers-nucleic acid/drug complex to bind to specific target cells and penetrate into such cells (tumor cells, liver cells, hematopoietic cells, and the like). The target ligands can also be an intracellular targeting element, enabling the transfer of the nucleic acid/drug to be guided towards certain favored cellular compartments (mitochondria, nucleus, and the like). In a preferred embodiment, the ligands can be sugar moieties coupled to the amino groups.

Such sugar moieties are preferably mono- or oligo-saccharides, such as galactose, glucose, fucose, fructose, lactose, sucrose, mannose, cellobiose, nytrose, triose, dextrose, trehalose, maltose, galactosamine, glucosamine, galacturonic acid, glucuronic acid, and gluconic acid. The galactosyl unit of lactose provides a convenient targeting molecule for hepatocyte cells because of the high affinity and avidity of the galactose receptor on these cells.

Other types of targeting ligands that can be used include peptides such as antibodies or antibody fragments, cell receptors, growth factor receptors, cytokine receptors, folate, transferrin, epidermal growth factor (EGF), insulin, asialooorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like.

Molecular weight analysis of the biodegradable cross-linked lipopolymer using intrinsic viscosity measurement revealed an apparent molecular weight of 7.5 kD against linear polyethylenimine standards (Table I). Intrinsic viscosity (and light scattering) actually measures effective gyrational radius of polymer molecule, which is dependent on molecular weight and on the shape of the molecule (Introduction to Physical Polyemr Science, 3$^{rd}$, Leslie Howard Sperling Wiley, 2001, page 96-102). From linear calibration curve it appears that LPEI molecules are tending to "rod shape" in aqueous solution at pH 2.5. For branched PEIs one has to incorporate "shape factor", >1, accounting for more dense packing of polymer molecule into the same gyrational radius. Thus actual molecular weight of branched PEI is higher than apparent value as measured against linear PEI standard by the shape factor value. This is illustrated below by linear molecule of 2 units versus arbitrarily drawn moderately branched 3 unit molecules the shape factor can be very high. From the data on biodegradable cross-linked polymer transfection activity (FIG. 8) it appears that the shape factor is rather low, 1.5-2, thus the measured oligomer is in all probability closer to a trimer molecule.

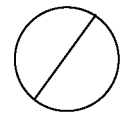 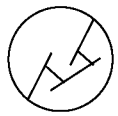

Linear molecules of 2 units    Moderately branched molecule of 3 units

Figure 5:
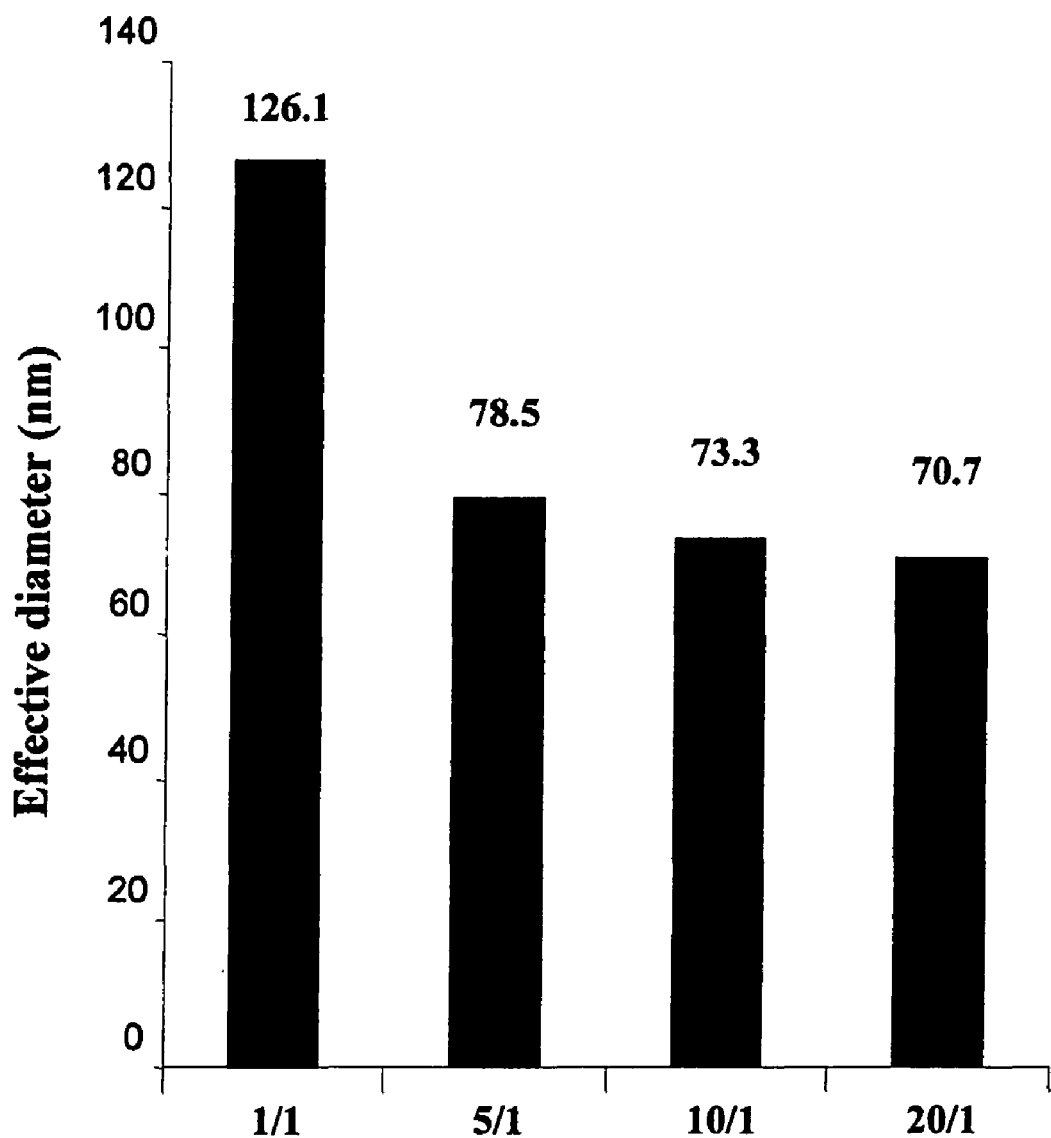
FIG. 5 shows the particle size of DNA complexes with biodegradable, cross-linked, cationic multi-block lipopolymers of LPEI 3.6 kD (BD3.6K-O) at various N/P ratios.
Figure 6:
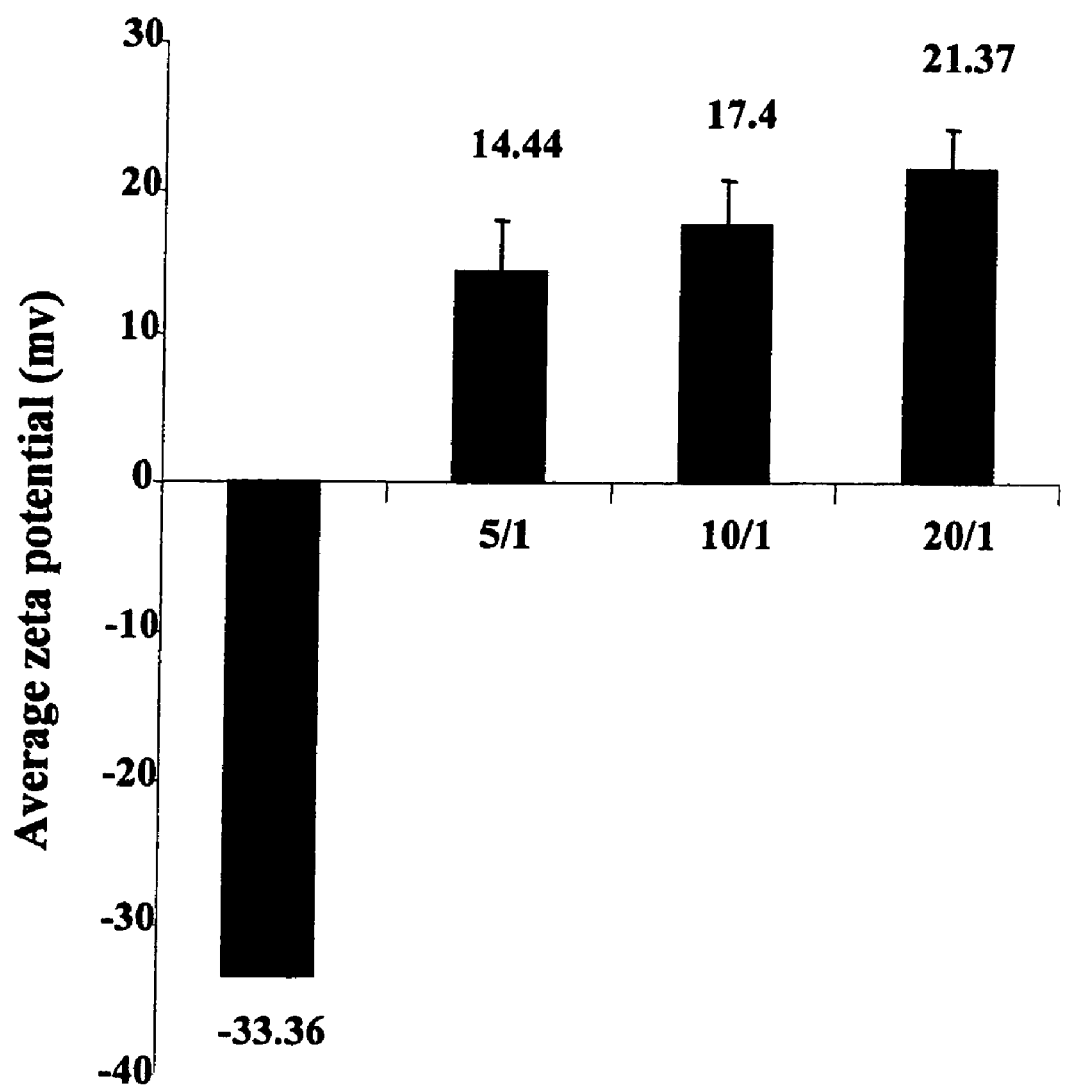
FIG. 6 shows the zeta potential of DNA complexes with biodegradable, cross-linked, cationic multi-block lipopolymer of LPEI 3.6 kD (BD3.6K-O) at various N/P ratios.

An advantage of the present invention is that it provides a gene carrier wherein the particle size and charge density are easily controlled. Control of particle size is crucial for optimization of a gene delivery system because the particle size often governs the transfection efficiency, cytotoxicity, and tissue targeting in vivo. In the present invention, the particle size is shown to be around 100 nm diameter (FIG. 5), which is an efficient particle size to entry into cells via endocytosis. In addition, positively charged particle surfaces provide for a sufficient chance of binding to negatively charged cell surfaces, followed by entry into cells by endocytosis. The gene carriers disclosed in the present invention have a zeta-potential in the range from +10-+20 mV (FIG. 6).

The cationic multi-block copolymers of the present invention are suitable for the delivery of macromolecules such as DNA into mammalian cells. The ability to condense the large and negatively charged DNA molecule into small (<200 nm)

and positively charged nanoparticles is considered a crucial step in the gene transfer by cationic polymers. The particle size and zeta potential of the cationic polymer/DNA complexes is influenced by the nitrogen to phosphate (N/P) ratio between the polymer and the DNA molecules in the polymer/DNA complexes. The experiments and results presented below demonstrate that the physico-chemical properties of the biodegradable polymer are compatible with its use as a safe and efficient gene delivery system.

Figure 7:
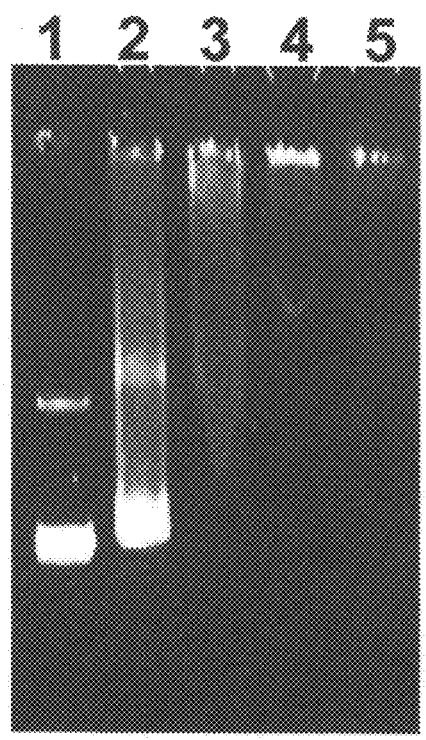
FIG. 7 shows the electrophoretic mobility of DNA complexes with biodegradable, cross-linked, cationic multi-block lipopolymers of LPEI 3.6 kD (BD3.6K-O) at various N/P ratios.

The ability of the biodegradable cross-linked cationic multi-block copolymers of this invention to condense the DNA molecule into small particles was examined using gel electrophoresis and particle sizing. The electrophoretic mobility of plasmid DNA before and after the addition of increasing concentrations of biodegradable, cross-linked, cationic multi-block copolymers is shown in FIG. 7. The degree of DNA complexation with the polymer improved as the ratio between the polymer and DNA was increased. The optimal condensation was achieved at N/P ratios between 5/1 to 10/1. The mean diameter of the polymer/DNA complexes was under 200 nm, a suitable size distribution for endocytotic uptake of the complexes by target cells.

Figure 8:
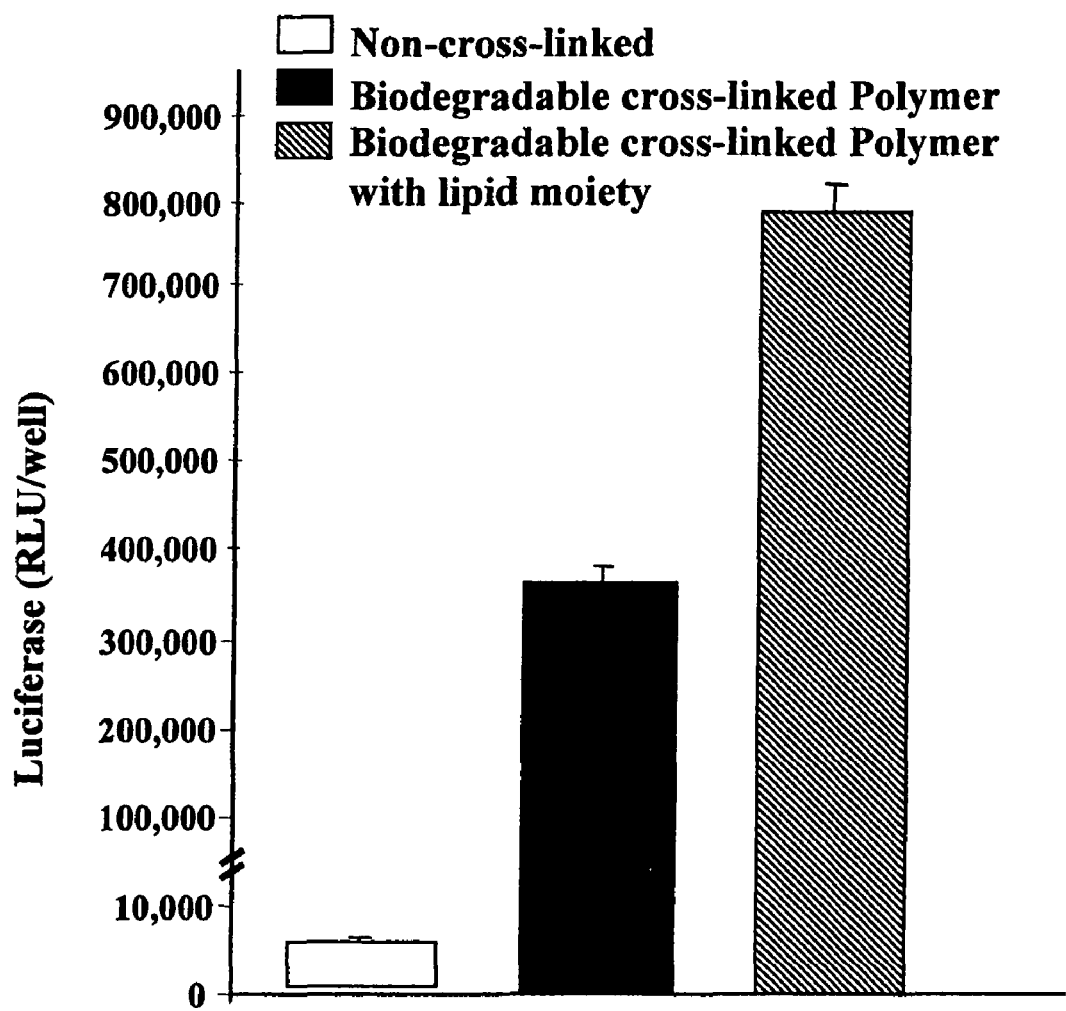
FIG. 8 shows in vitro gene transfer using biodegradable, cross-linked, cationic, multi-block copolymers (BD3.6K) and biodegradable, cross-linked, cationic, multi-block lipopolymers of LPEI 3.6 kD (BD3.6K-O) and non-cross-linked single PEI 3.6 kD block polymers.
Figure 9:
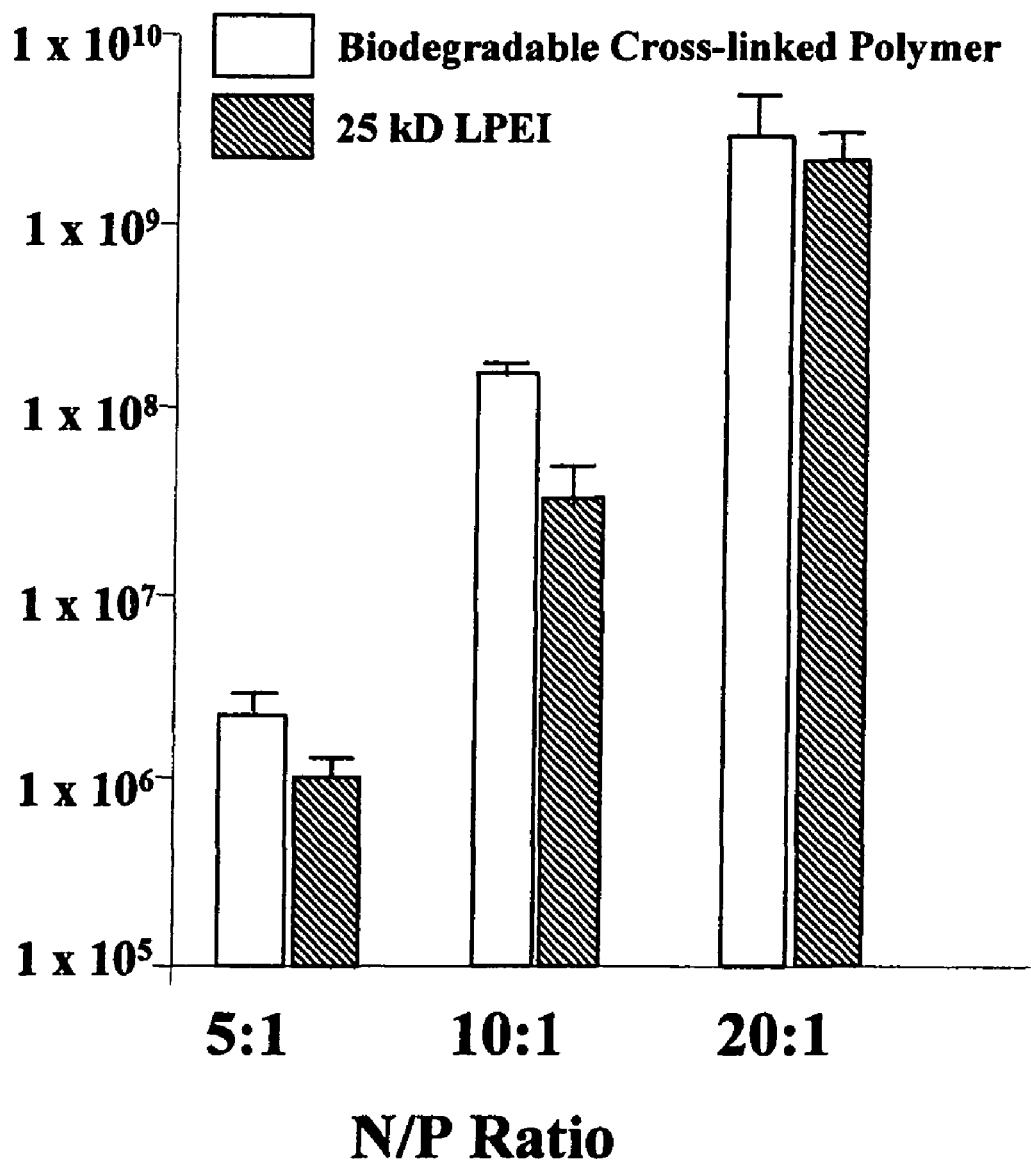
FIG. 9 shows in vitro gene transfer using biodegradable, cross-linked, cationic multi-block lipopolymers of linear PEI 3.6 kD (BD3.6K-O) and 25 kD linear PEI.

The DNA complexes of the biodegradable multi-block copolymer are transfectionally active in mammalian cells. A comparison of the transfection efficiencies of the biodegradable cross-linked cationic multi-block copolymer gene carriers of the present invention to that of the basic structural polymer block is illustrated in FIG. 8. Approximately a 70-fold improvement in expression was made when using the biodegradable polymeric carrier. Covalent attachment of a lipid moiety to the biodegradable multiblock copolymer further enhanced the gene transfer efficiency with a total enhancement of 140 fold over the basic structural polymer block (FIG. 8). In a different type of assay where the gene transfer is quantified as percent of the total number of cells exposed to the transfection complexes, the biodegradable cross-linked cationic multi-block copolymers routinely transfected 75-90% of the target cells. The transfection activity and cytotoxicity of the biodegradable cross-linked multi-block copolymer was compared with that of 25 kD linear PEI at various N/P ratios. As shown in FIG. 9, the transfection activity at all test N/P ratios was significantly higher from the biodegradable cross-linked copolymers than that from the 25 kD linear PEI. These data demonstrate that the cross-linking scheme described in the present invention dramatically enhances the transfection activity of small molecular weight linear PEI (3.6 kD) to levels achieved with a much higher molecular weight linear PEI (25 kD).

Figure 10:
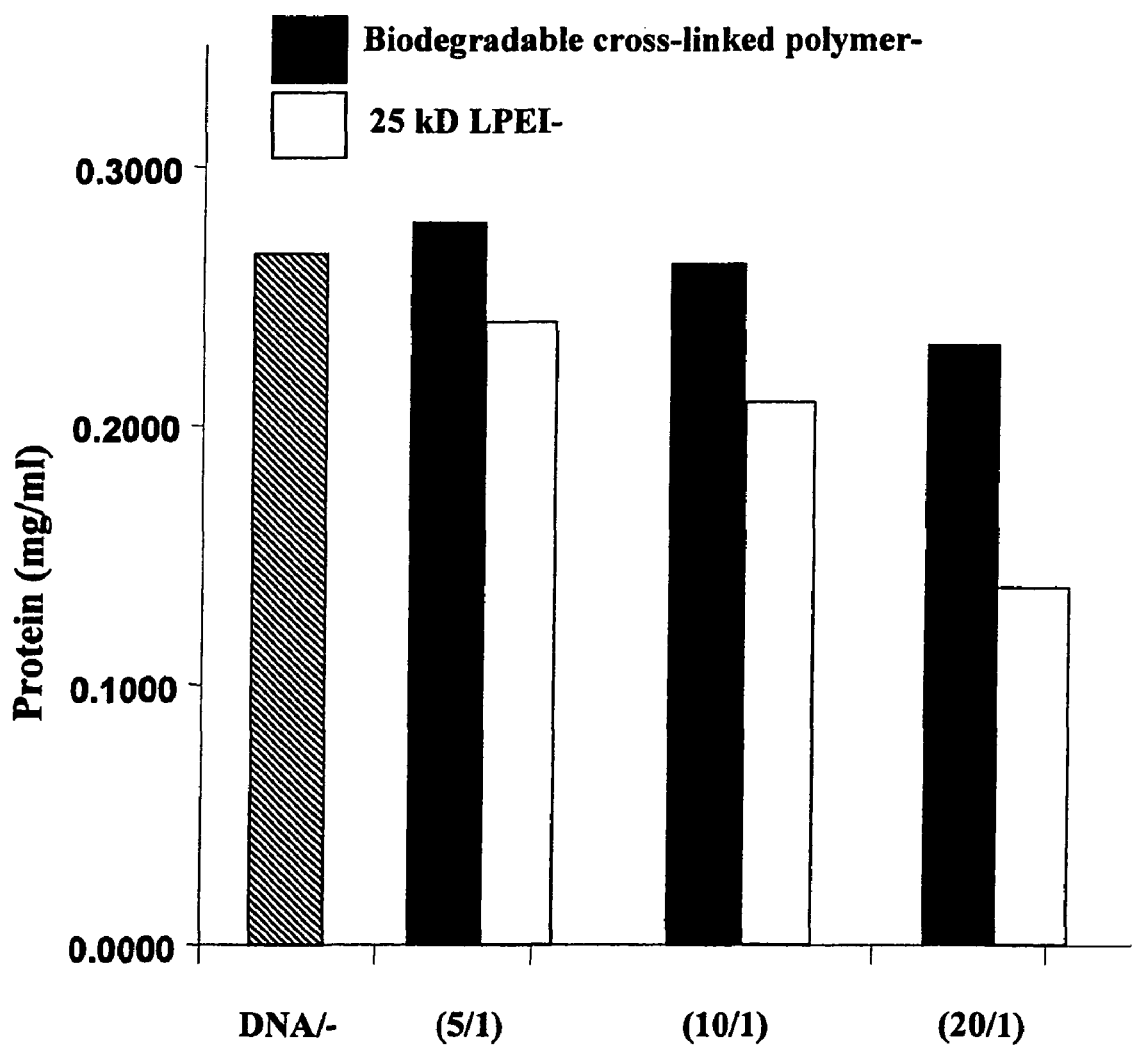
FIG. 10 shows the resultant cytotoxicity after gene transfer using biodegradable, cross-linked, cationic multi-block lipopolymers of linear PEI 3.6 kD (BD3.6K-O) and linear PEI 25 kD.
Figure 11:
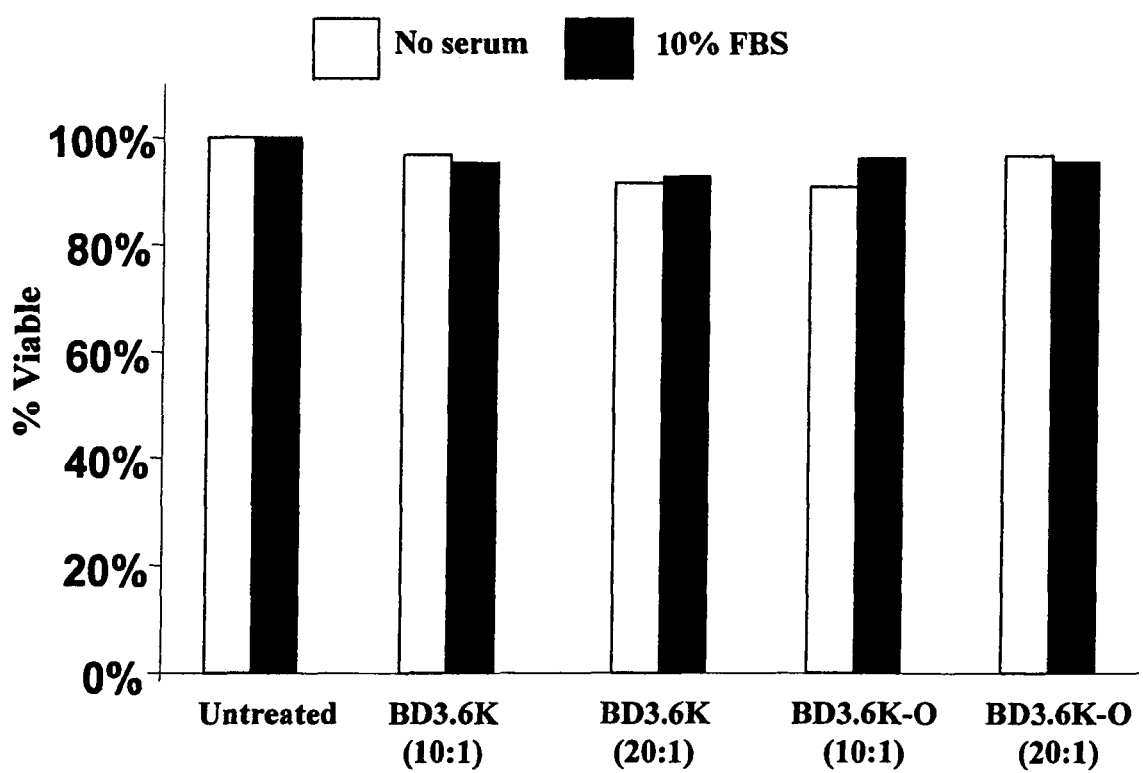
FIG. 11 shows cell viability after gene transfer using biodegradable, cross-linked, cationic multi-block copolymers of linear PEI 3.6 kD (BD3.6K) and biodegradable cross-linked lipopolymers of LPEI 3.6 kD (BD3.6K-O) in Cos-1 cells.

Cell viability or cytotoxicity is an important parameter when determining the usefulness of gene carriers. As previously stated, high transfection efficiency of cationic polymers is often associated with high cytotoxicity. The cytotoxicity of the biodegradable cross-linked cationic multi-block copolymers was examined in Cos-1 cells alongside with 25 kD PEI. As shown in FIG. 10 and FIG. 11, incubation of Cos-1 cells with transfection complexes containing luciferase plasmid and the biodegradable cross-linked cationic multi-block copolymers of the present invention resulted in only minor cytotoxicity compared to that seen with 25 kD linear PEI. These data demonstrate that coupling of small molecular weight linear PEI via small biodegradable linkages using the scheme described in the present invention dramatically enhances the polymer transfection activity without significantly increasing cytotoxicity.

Figure 12:
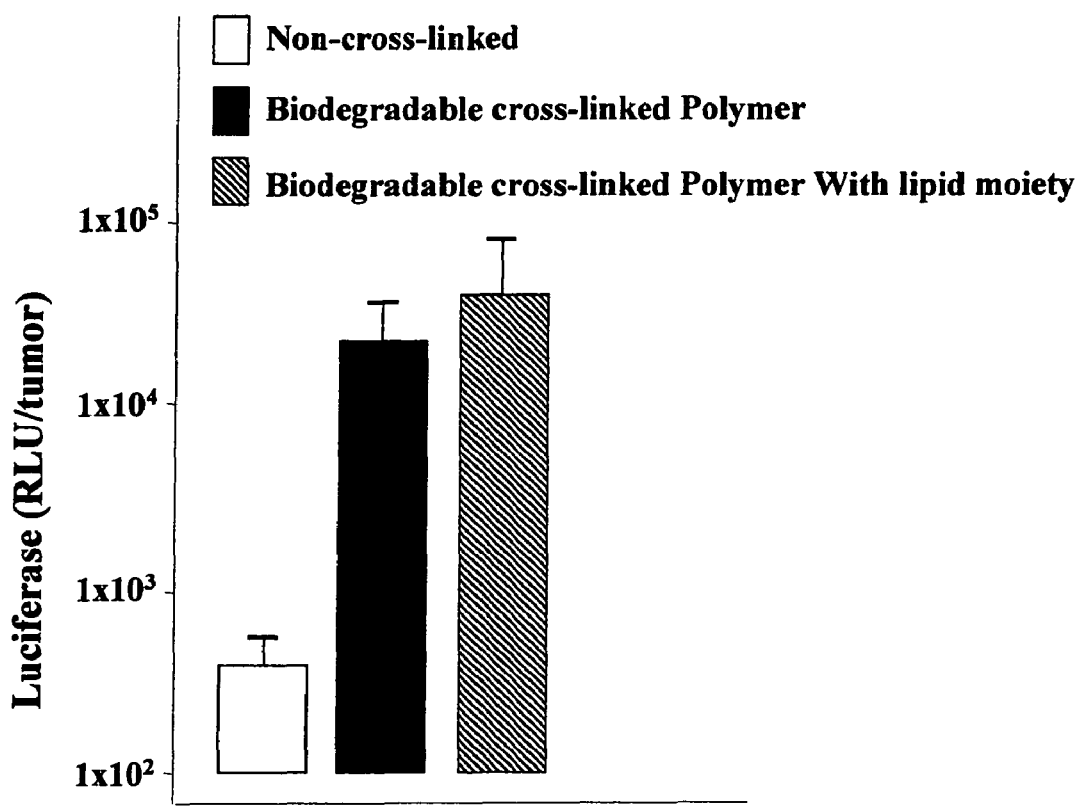
FIG. 12 shows in vitro gene transfer using biodegradable, cross-linked, cationic multi-block lipopolymers of linear PEI 3.6 kD (BD3.6K-O) in 4T1 tumors.

In order to evaluate the ability of the biodegradable cross-linked cationic multi-block copolymers to work in vivo, a murine tumor model was incorporated. For these studies syngenic mouse strains were implanted with murine mammary carcinoma cells. Following a period of growth the tumors were injected with luciferase plasmid complexed with the biodegradable polymeric carriers. Twenty-four hours after treatment the tumors were removed and homogenates were analyzed for protein expression (FIG. 12). Both of the biodegradable cross-linked cationic multi-block copolymers (with and without the lipid moiety) were able to transfect tumor tissue, demonstrating therapeutic potential of these polymers for gene therapy of human diseases.

Figure 13:
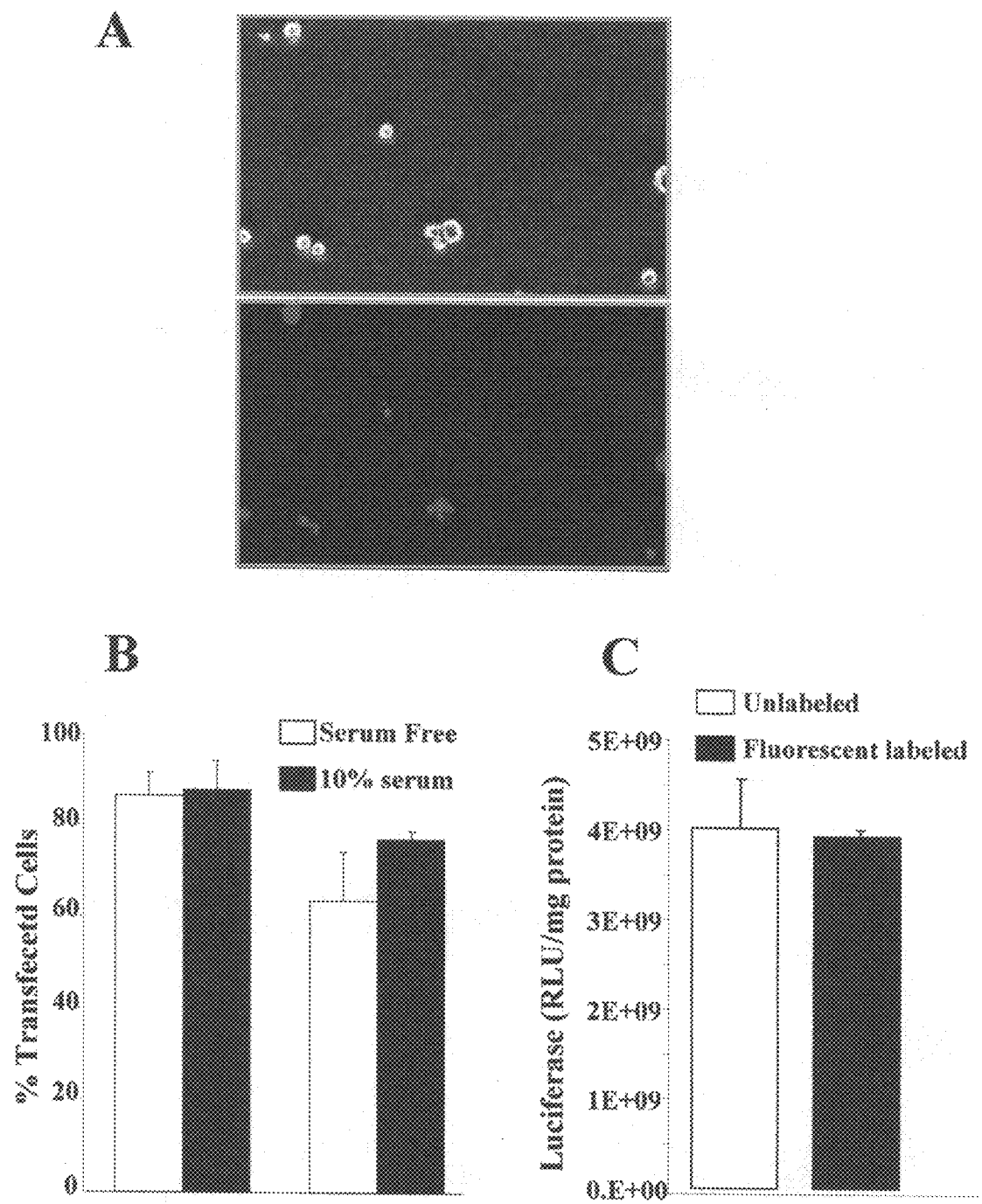
FIG. 13 shows the use of fluorescent-labeled biodegradable, cross-linked, cationic multi-block lipopolymers of linear PEI 3.6 kD (BD3.6K-O) for gene transfer and cellular localization of the polymer/DNA complexes.

To aid in cellular localization of transfection complexes a fluorescent rhodamine was covalently attached to the biodegradable cross-linked cationic multi-block copolymers. The fluorescent-labeled biodegradable multiblock copolymers were complexed with β-galactosidase plasmids and added to Cos-1 cell cultures for 4 hours. Fluorescent microscopy of cells transfected with labeled polymer shows a near 100% uptake by Cos-1 cells (FIG. 13, panel A). The fluorescent labeling of the biodegradable multiblock copolymer did not affect gene transfer when compared with the unlabeled polymer/DNA complexes both in the presence or absence of fetal bovine serum (panel B). Similar results were obtained when the fluorescent-labeled polymer was used with luciferase plasmid (panel C).

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

Example 1

Synthesis of Linear Polyethylenimine

This example illustrates the preparation of linear polyethyleneimine polymer blocks of the present invention, in form of sulfate salts (FIGS. 1, 2).

These materials were prepared by a slightly modified Tanaka's procedure.

*Macromolecules,* 1983, vol 16, 849-853

1. Purification of Monomer.

Commercial 2-phenyloxazoline is usually colored (yellow-green to brown) and was distilled in a vacuum (bp 110°/8 mmHg) to obtain a colorless material. To 300 g of such distillate was added about 45 g of ground (powder) KOH, and the mixture placed in a 500 mL flask. The flask was connected to a rotary evaporator and was then rotated in a 50° C. bath at atmospheric pressure for 4-5 hrs. Yellowish coloration developed. The mixture was filtered through a sintered glass funnel; the solid cake was washed with a small amount of methylene chloride, and then discarded. The filtrates were washed with water (2×100-150 mL), and then dried over $Na_2SO_4$. To the dried liquid was added 1 g of benzoyl chloride and the mixture was distilled (first methylene chloride was removed at 760 mm, then a small cloudy forerun (bp<100°/8) with the strong smell of benzonitrile, and then purified phenyloxazoline was collected at 110°/8 mmHg). It can be stored over $Na_2SO_4$ under argon atmosphere, at least for a few days. Recovery rate is about 90%.

2. Polymerization: poly (N-benzoylethyleneimine).

A specially made sealable vial was charged with 100 g (680 mMol) of purified phenyloxazoline and 0.62 g of $Me_2SO_4$. The mixture was swirled to ensure mixing, and the vial connected to a vacuum/Ar manifold and placed in a cooling bath.

As soon as the mixture solidifies, the vial was then placed in a warm water bath. The mixture was allowed to melt and degas under vacuum and the vial sealed while under vacuum. The sealed vial was then placed in a hot bath (140° C.; however, for larger catalyst loadings the polymerization can proceed violently, and lower bath temperatures (120° C.) may be advisable, at least in the beginning of polymerization). The vial was maintained at 140° C. for 48 hrs, during which time the mixture solidifies. The vial was then removed from the hot bath, cooled and broken. The brittle polymer was broken into small pieces and ground into a powder. It appears that the chunks of even 8-10 mm size slowly hydrolyze and disperse upon stirring in hot acid during the next step, thus fine grinding may be unnecessary. Recovery is 98-99 g with a MW of 12K determined by GPC vs. polystyrene standards. Polymers of different MW (8K to 51K) were prepared in this way using different amounts of catalyst.

3. Debenzoylation: Linear Polyethyleneimine Sulfate.

A 1 liter-round bottom flask was charged with about 50 g of poly(N-benzoylethyleneimine), water (180 mL) and concentrated $H_2SO_4$ (300 g). The flask was equipped with a 1" egg-shaped magnetic stirring bar and an (air) reflux condenser. The flask is placed in a 140-145° C. heating bath and the mixture was heated and stirred. Initially the polymer forms a viscous mass which soon became a cloudy dispersion; (energetic mixing is a must). The heating and stirring were continued for about 20 hrs. The stirring was then stopped; molten benzoic acid forms a (top) separate layer. The hot lower layer was then transferred into another flask using a large pipette; on cooling it solidifies, thus the transfer has to be done rapidly. This solidified lower layer diluted with water (about 400 mL) and any residual benzoic acid was removed by steam distillation. As an added test: the hot pot liquid should become transparent before the end of steam distillation. The presence of solids at this point indicated incomplete debenzoylation. On cooling the pot liquid separates turned white to off-white crystals of polyethyleneimine sulfate (hydrate); these were collected by filtration, washed on a filter with water, then with acetone, and then dried. Recovery is about 33 g (97%).

The material obtained from benzoyl-LPEI with a MW of 51K has NMR ($D_2SO_4$, $Me_3SiCD_2CD_2CO_2Na$ as a standard) corresponding to its claimed structure: δ3.62 (s, $CH_2$ groups); 6.4-8.2 (small traces of benzoyl groups). Elemental analysis (Galbraith Laboratories): C, 22.37%; N, 12.54%, S, 16.58% Calculated for ($-CH_2NHCH_2CH_2NHCH_2-\times 1H_2SO_4 \times 1H_2O$) C, 23.75%; N, 13.87%, S, 15.85%. A small sample of this material was re-benzoylated (non-exhaustively) and had an MW of 45K, indicating that no significant backbone degradation occurred under the harsh hydrolysis conditions.

Example 2

Synthesis of a Biodegradable Multiblock Cationic Polymer

This example illustrates the preparation of a biodegradable multi-block copolymer of 3.6 kD linear PEI (BD3.6K) (FIGS. 3, 4).

1. Linear Polyethyleneimine Free Base.

A 2 L Erlenmeyer flask was equipped with a magnetic stirrer and charged with LPEI (Mw 3.6 kD) sulfate hydrate (30 g, about 0.15 Mol $SO_4^{2-}$), and water (1 L). To the stirred mixture was added NaOH (20 g, 0.5 Mol) and the heterogeneous mixture was warmed to 50-60° C. and stirred for 3 hrs. The mixture was cooled; the precipitated LPEI hydrate was filtered, washed with water, and dried.

2. $LPEI_{3600}BOC_{95\%}$

A pre-tarred 250 mL flask was charged with LPEI free base hydrate (7.1 g) and connected to a vacuum line. The vacuumized flask was heated to 75° C. in an oil bath. LPEI hydrate slowly converted into a melt of anhydrous LPEI with bubbling. After 3 hrs of heating under vacuum, the brown LPEI melt was cooled, and the flask was flushed with argon. 5.4 g (125 mMol of N) of anhydrous LPEI was obtained. To the flask with LPEI was added 120 mL of dry chloroform and a magnetic stirring bar. The mixture was stirred under argon till the LPEI melt dissolved, forming a slightly cloudy solution. To this stirred solution was added t-Butoxycarbonyl(BOC) anhydride (26 g, 119 mMol, 95%) over 10 min. The addition was accompanied by mild exotherm and gas evolution. The mixture was further stirred for 3 hrs, the small amount of suspended particulates was filtered out, and the mixture was concentrated in a vacuum. Recovery is 17 g. with a MW about 11700 (by GPC against polystyrene standards).

3. LPEI-Linker Conjugates.

A vial was equipped with a magnetic stirrer and charged with 2.3 g (197 μMol) of $LPEI_{3600}BOC_{95\%}$ and 5 mL of dry chloroform. The mixture was warmed and stirred to dissolution, and 150 mg (600 μMol) of dithiodipropionyl chloride (obtained from commercial dithiodipropionic acid and thionyl chloride) in 0.5 mL of chloroform was slowly added to the stirred mixture over 10 min. The stirred mixture was kept at room temperature for several days until there was strong gelling. At this point 10 mL of trifluoroacetic acid was added and the mixture was stirred for 30 min. The lower (brown) layer of the resulting heterogeneous mixture was withdrawn, and diluted with 40 mL of water. Residual chloroform and a small amount of particulate impurities were removed by centrifugation. An aqueous solution of $Na_2SO_4$ (3 g) in 10 mL of water was added to the supernatant, and the resulting precipitate of the linked LPEI (BD3.6K) sulfate was collected, washed with water, then with acetone, and dried. The yield was 1.2 g of off-white material.

A 50 mL flask was charged with 1.2 g BD3.6K sulfate (about 520 mg sulfate) and 30 mL water. $BaCl_2$ dihydrate (1200 mg, 90% theory) was added and the heterogeneous mixture was vigorously stirred for 48 hrs. Barium sulfate was then filtered off, the aqueous filtrate was further filtered through a 0.2 μm syringe filter, and the aqueous filtrate was then concentrated under vacuum to about a volume of 6 mL. Upon dilution with 200 mL of acetone, linked LPEI chloride precipitated, was filtered, washed with acetone, and dried. The amount collected was about 0.9 g.

Alternatively, gelled BOC-protected material can be deprotected by treatment with an excess of HCl/dioxane solution. Vacuum concentration of the deprotected reaction mixture and THF trituration of the solid residue directly produces the target material in hydrochloride form.

Example 3

Synthesis of a Lipid Conjugate of the Biodegradable Multi-Block Cationic Polymer This example illustrates the preparation of lipid conjugates of biodegradable cross-linked cationic multi-block copolymers. The biodegradable multi-block copolymers of 3.6 kD linear PEI (BD3.6K) were conjugated with the lipid oleoyltetraethyleneglycolcarbonyl to form BD3.6K-Oleoyl (BD3.6K-O).

A vial was equipped with a magnetic stirrer and charged with 2.3 g (197 μMol) of $LPEI_{3600}BOC_{95\%}$ and 6 mL of dry chloroform. The mixture was warmed and stirred to achieved dissolution, and 150 mg (600 μMol) of dithiodipropionyl chloride (obtained from commercial dithiodipropionic acid and thionyl chloride) in 1.2 mL of chloroform and 110 mg (about 200 μMol) of oleoyltetraethyleneglycolcarbonyl chloride (obtained from commercial polyethylene-glycol monooleoyl ester and phosgene) in 1.2 mL of chloroform were slowly added to the stirred mixture over 10 min. The stirred mixture was kept at room temperature for several days until there was strong gelling. At this point, 10 mL of trifluoroacetic acid was added and the mixture was stirred for 30 min. The lower (brown) layer of the resulting heterogeneous mixture was withdrawn, and diluted with 40 mL of water. Residual chloroform and the small amount of particulate impurities were removed by centrifugation. An aqueous solution of $Na_2SO_4$ (3 g) in 10 mL water was added to the supernatant, and the resulting precipitate of linked functionalized LPEI (BD3.6K-O) sulfate was collected, washed with water, then with acetone, and dried. The yield was 1.35 g of off-white material.

A 50 mL flask was charged with 1.3 g (BD3.6K-O) sulfate (about 550 mg sulfate) and 30 mL water. $BaCl_2$ dihydrate (1.25 g, 90% theory) was added and the heterogeneous mixture was vigorously stirred for 48 hrs. Barium sulfate was then filtered off, the aqueous filtrate was further filtered through 0.2 μm syringe filter, and the aqueous filtrate was then concentrated under vacuum to about a volume of 6 mL. Upon dilution with 200 mL of acetone, (BD3.6K-O) chloride precipitated, was filtered, washed with acetone, and dried. The amount collected was 0.9 g.

Alternatively, gelled BOC-protected material can be deprotected by treatment with an excess of a HCl/dioxane solution. Vacuum concentration of the deprotected reaction mixture and THF trituration of the solid residue directly produces the target material in hydrochloride form.

Example 4

Synthesis of the Lipid Conjugate of a Biodegradable Multi-Block Cationic Polymer Covalently Linked to a Fluorescent Marker This example illustrates the preparation of fluorescent-labeled lipid conjugates of biodegradable cross-linked cationic multi-block copolymers. The biodegradable multiblock lipopolymer of Example 3 (BD3.6K-O) was labeled with the fluorescent marker rhodamine.

A vial was equipped with a magnetic stirrer and charged with 1.86 g (156 μMol) of $LPEI_{3600}BOC_{95\%}$ and 5 mL of dry chloroform. The mixture was warmed and stirred to achieve dissolution. The fluorescent marker lissamine sulfonylchloride (9 mg, about 15 μMol in 1 mL $CHCl_3$) and 120 mg (470 μMol) of dithiodipropionyl chloride in 0.5 mL of $CHCl_3$ and 85 mg (about 160 μMol) of oleoyltetraethyleneglycolcarbonyl chloride in 0.5 mL of $CHCl_3$ were slowly added to the stirred mixture over 10 min. The stirred mixture was further concentrated under vacuum to a volume of 6 mL, and was placed in a 50° C. bath for several days until there was strong gelling. After 48 hrs, the mixture was diluted with 100 mL of petroleum ether and the sold material was collected by filtration and washed on a filter with acetone until the filtrates were almost colorless and dried. To the dry material 5 mL of $CHCl_3$ and 5 mL of trifluoroacetic acid were added and the mixture was stirred for 90 min. The lower (brown) layer of the heterogeneous mixture was withdrawn, and diluted with 40 mL of water. Residual chloroform and a small amount of particulate impurities were removed by centrifugation. An aqueous solution of $Na_2SO_4$ (3 g) in 10 mL of water was added to the mixture, and the resulting precipitate of linked functionalized LPEI sulfate was collected, washed with water, then with acetone, and dried. A significant amount of unconjugated rhodamine (purple dye) was removed during washing, probably indicating sulfonylchloride hydrolysis. About 1.4 g of purple material was obtained.

A 50 mL flask was charged with 1.4 g of labeled LPEI conjugate (about 550 mg sulfate) and 30 mL water. $BaCl_2$ dihydrate (1.4 g, about 95%) was added and the heterogeneous mixture was vigorously stirred for 48 hrs. The barium sulfate was then filtered off, the aqueous filtrate was further filtered through a 0.2 μm syringe filter, and the aqueous filtrate was then concentrated in a vacuum to a volume of 5 mL. Upon dilution with 200 mL of acetone, linked functionalized LPEI chloride precipitated, was filtered, washed with acetone, and dried. The amount collected was about 0.9 g.

Example 5

Estimation of the Molecular Weight of Biodegradable Multiblock Cationic Polymer Solutions of LPEI hydrochloride and of biodegradable cross-linked multi-block polymer (at precisely measured concentrations in the range of 5 mg/ml, pH ~2.5) in distilled water were prepared. In an immersion bath (large beaker filled with water, at 21° C.) was placed a Cannon-Fenske routine viscometer and the flowing times of fixed volume of these solutions and of the solvent (distilled water) through a capillary tube of viscometer were measured. The dimensionless ratio of a solution flow time to solvent flow time was recorded as relative viscosity. The ratio of relative viscosity to the concentration of solution (measured in g/dl) was taken as intrinsic viscosity (more strictly speaking, it should be measured as the limiting value at infinite dilution). This value (g/dl) was plotted against molecular weight of LPEI polymers, as previously measured from GPC of precursor poly (N-benzoylethyleneimines) versus polystyrene standards. The result of viscosity measurements and molecular weight analysis are described in Table I.

TABLE I

| Material | conc | time (sec) | rel. time | MW | intr. n = t/c |
|---|---|---|---|---|---|
| Water (ref) | | 274.4 | 1 | | |
| LPEI 3.6 | 52/100 | 316.1 | 1.153 | 3600 | 2.28 |
| LPEI 7.5 | 51/100 | 387 | 1.41 | 7500 | 2.77 |
| LPEI 11 | 51.7/101 | 451.3 | 1.645 | 11000 | 3.22 |
| LPEI 15 | 51/100 | 517.6 | 1.886 | 15100 | 3.69 |
| BD3.6K-O | 51/100 | 387.2 | 1.41 | 7500 | 2.77 |

Example 6

Amplification and Purification of a Plasmid

This example illustrates the preparation of DNA to be used to complex with the biodegradable cross-linked cationic multi-block copolymers of the present invention. The plasmid encoding for luciferase protein and the plasmid encoding for β-glactosidase (β-Gal) protein were amplified in JM109 *E. coli* strains and then purified using Qiagen EndoFree Plasmid Maxi-prep or Giga-prep kits (Chatsworth, Calif.) according to the manufactures instructions. Following purification, the DNA concentration was determined spectrophotometrically using an absorbance of 260 nm. Plasmid DNA integrity was evaluated using agarose gel electrophoresis followed by ethidium bromide staining.

Example 7

Preparation of Water-Soluble Complexes of DNA with Biodegradable Cross-Linked Cationic Multi-Block Copolymers This example illustrates the formation of BD3.6K-O/DNA complexes. The BD3.6K-O polymer was dissolved in sterile water to give a final concentration of 3 mg/ml. The DNA was dissolved in sterile water to give a final concentration of 1 mg/ml. To make the polymer/DNA complex, the two components were diluted separately with 5% glucose to a volume of 150 µL each, and then the plasmid DNA solution was added to the polymer solution. Complex formation was allowed to proceed for 15 minutes at room temperature. To study the effect of the charge ratio on gene transfer, BD3.6K-O/DNA complexes were prepared at different ratios 1/1, 5/1, 10/1, and 20/1 nitrogen/phosphate (N/P). Following complex formation, the complexes were diluted in a cuvette for measurement of particle size (FIG. 5) and the $\zeta$ potential (FIG. 6) of the complex. The electrophoretic mobility of the samples was measured at 25° C., and at a wavelength of 657 nm and at a constant angle of 90° with a 90Plus/BI-MAS Particle sizer with BI-Zeta option (Brookhaven Instruments Corp., Holtsville, N.Y.).

Example 8

Gel Retardation Assay

The ability of BD3.6K-O polymers to condense plasmid DNA was evaluated in this example (FIG. 7). Briefly BD3.6K-O was complexed with plasmid DNA at various N/P ratios (1/1, 5/1, 10/1, 20/1) in the presence of 5% glucose (w/v). The complex was electrophoresed on a 1% agarose gel. The positively charged BD3.6K-O polymer formed a strong complex with the negatively charged phosphate ions on the sugar backbone of DNA. When the N/P ratio reached (10/1) no free DNA was seen.

Example 9

In Vitro Gene Transfer

This example shows in vitro gene transfer using the DNA complexes with biodegradable cross-linked multi-block copolymers of the present invention (FIGS. 8, 9). Transfection complexes containing luciferase plasmid, pCMV-Luc, and BD3.6K-O or high molecular weight LPEI (25 kD) were prepared at different polymer/DNA (N/P) ratios in Dulbecco's modified Eagle's medium (DMEM) and tested for luciferase gene transfer in cell cultures. Cos-1 cells ($1.5 \times 10^5$) were seeded to 80% confluency in 12-well tissue culture plates in 10% FBS. Transfection complexes containing 1 g of plasmid DNA were added into each well in the presence or absence of 10% fetal bovine serum for 6 hours in a $CO_2$ incubator. The transfection medium was removed and the cells were incubated for 40 hours with 1 ml of fresh DMEM containing 10% FBS. The cells were washed with phosphate-buffered saline and lysed with TENT buffer (50 mM Tris-Cl [pH 8.0], 2 mM EDTA, 150 mM NaCl, 1% Triton X-100). Luciferase activity in the cell lysate was measured as relative light units (RLU) using an Orion Microplate Luminometer (Berthold Detection systems USA, Oak Ridge, Tenn.). The final values of luciferase were reported in terms of RLU/mg total protein. A total protein assay was carried out using a BCA protein assay kit (Pierce Chemical C, Rockford, Ill.).

The above protocol was also used for β-galactosidase gene transfer. The levels of β-galactosidase gene transfer was quantified with a X-Gal staining assay kit obtained from Gene Therapy Systems, Inc. (San Diego, Calif.)

Example 10

Cytotoxicity

This example gives the steps involved in the cytotoxicity screening of the biodegradable cross-linked multi-block copolymers using DNA complexes with BD3.6K-O at different nitrogen to phosphate ratios (FIGS. 10, 11). The cytotoxicity of transfection complexes was assessed by a total protein assay and a cell proliferation assay (Promega Corporation, 2800 Woods Hollow Road, Madison, Wis. 53711-5399). The protein assay is described in Example 8.

Cos-1 (African Green Monkey Kidney cells) were grown and maintained in DMEM medium supplemented with 10% fetal bovine serum, 1% penicillin, 1% streptomycin and glutamine. The cells were kept in a 37° C. humidified 5% $CO_2$ incubator.

Cos-1 cells were plated at a density of $1.5 \times 10^3$ cells/well in a 96 well plate and incubated overnight at 37° C. in 5% $CO_2$. After reaching 70-80% confluency, 0.1 µg of DNA was added to BD3.6K-O at varying charge ratios. Next, the BD3.6K-O/DNA complexes were added to wells divided into two groups: DMEM containing FBS and DMEM without FBS with both groups having a total volume of 100 L in each well. The serum free wells were incubated for 5-6 hours, the media was aspirated off, then normal growth media without antibiotics was added. The wells containing FBS were incubated for 24 hours, and an equal volume of serum containing media was added (without antibiotics). After both groups were incubated for 48 hours after transfection, the media was aspirated from all wells, and 100 µL normal growth media (without antibiotics) was added to all of the wells. Next, 20 µL of room temperature CellTiter 96® $AQ_{ueous}$ One Solution Reagent was added to each well and the plate was incubated for 4 hours. After the incubation period, the plate was spectrophotometrically read at 490 nm on an ELISA plate reader. The relative percent cell viability was calculated using the following equation:

Viability (%)=$OD_{490}$(sample)/$OD_{490}$(control)×100

The $OD_{490}$(control) represents the measurement from the wells treated with growth media only and the $OD_{490}$(sample) represents the measurement from the wells treated with varying ratios of BD3.6K-O/DNA.

A side by side comparison of BD3.6K-O and 25 KD LPEI in a protein based cytotoxcity assay demonstrates lesser cotytoxicity of BD3.6K-O (FIG. 10). The cytotoxcity of BD3.6K and its lipid derivative BD3.6K-O was also examined in a cell viability assay. As shown in FIG. 11, exposure of Cos-1 cells to the transfection complexes containing BD3.6K or BD3.6K-O did not affect cell viability.

Example 11

In Vivo Gene Transfer

This example illustrates in vivo gene expression using the biodegradable cross-linked multi-block copolymer for plasmid delivery (FIG. 12). The plasmid encoding for the luciferase protein was injected intra-tumorally into mice at a dose of 0.2 mg/ml total DNA complexed with the polymeric carrier BD3.6K-O at an N:P of 10:1 in a volume of 30 μl. This gave a 6 μg DNA dose per tumor. In this example, mammary carcinomas were induced into the left and right flanks of 7-8 week old BALB/c mice by the administration of $1\times10^6$ 4T1 cells (murine mammary carcinoma) in PBS that had been prepared in cell culture. After 10-11 days, when the tumor size reached approximately 70 mm$^3$ as calculated by the formula: volume=$\frac{4}{3}\times3.14\times(L/2\times W/2\times H/2)$ where L is the length of the tumor, W is the width and H is the height, the tumors were injected with the plasmid/polymer complex. One day later the tumors were removed and frozen using LN$_2$. The tumors were then homogenized in a lysis buffer and analyzed for luciferase activity using Promega's Luciferase Assay System (Madison, Wis.) according to the manufacturer's instructions using an Orion Microplate Luminometer (Berthold Detection Systems, Oak Ridge, Tenn.).

Example 12

Fluorescent Labeled Polymer: In Vitro Transfection/Analysis

This example shows the application of fluorescent labeled biodegradable cross-linked multi-block polymers in the cellular localization of transfection complexes and in vitro gene transfer (FIG. 13). Cos-1 cells were seeded in twelve well tissue plates at a cell density of $1.5\times10^5$/well in 10% FBS containing DMEM. The cells achieved 80% confluency 24 hours after being transfected with the BD3.6K-O/DNA complexes. The total amount of DNA loaded was maintained at a constant 1 μg/well and transfection was carried out in the presence of 10% FBS or in the absence of serum. The cells were incubated in the presence of the complex for 6 hours followed by replacement with 1 ml DMEM containing 10% FBS and incubated for an additional 40 hours. The expression levels of β-Gal were then evaluated using the X-Gal staining assay kit from Gene Therapy Systems, Inc (San Diego, Calif.).

For examination using fluorescent microscopy the cell transfection procedure was the same as for the β-Gal analysis except that after 2 hour incubation period with the BD3.6K-O/DNA, the medium was removed and the cells were washed with PBS and subsequently harvested using trypsin. The cells were then fixed, placed on slides and examined using an inverted fluorescent microscope. Fluorescent microscopy of cells transfected with labeled polymer shows a near 100% uptake by Cos-1 cells (FIG. 13, panel A). The fluorescent labeling of the biodegradable multiblock copolymer did not affect gene transfer when compared with the unlabeled polymer/DNA complexes both in the presence or absence of fetal bovine serum (panel B). Similar results were obtained when the fluorescent-labeled polymer was used with luciferase plasmid (panel C).

It is to be understood that the above-described embodiments are only illustrative of the applications of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

We claim:
1. A process for making a biodegradable water-soluble cross-linked poly(ethyleneamine), the process comprising:
    (a) protecting from about 90-95% of the amine nitrogens in a linear poly(ethylenimine) (LPEI) having a molecular weight of from about 1000 Da to about 25000 Da; and
    (b) cross-linking the protected LPEI with a cross-linking agent having a linear backbone of from 6-34 backbone members and a reactive group at each end of the backbone, where the backbone includes a disulfide bond.
2. A process according to claim 1, where the cross-linking is carried out at a molar ratio of cross-linking agent to protected LPEI of from 1:1 to 20:1.
3. A process for making a biodegradable water-soluble cross-linked poly(ethyleneimine), the process comprising:
    (a) protecting from about 90-95% of the amine nitrogens in a linear poly(ethylenimine) (LPEI) having a molecular weight of from about 1000 Da to about 25000 Da;
    (b) cross-linking the protected LPEI with a cross-linking agent having a linear backbone of from 6-34 backbone members and a reactive group at each end of the backbone, where the backbone includes a disulfide bond; and
    (c) reacting the protected cross-linked LPEI with an acylating agent comprising a fatty portion.
4. A process according to claim 3, where the cross-linking is carried out at a molar ratio of cross-linking agent to protected LPEI of from 1:1 to 20:1.
5. A process according to claim 3, further comprising (d) reacting the protected cross-linked LPEI with a targeting ligand.
6. A process according to claim 3 where (b) and (c) are carried out in one pot.
7. A process according to claim 3 where the acylating agent comprises a fatty portion coupled to an acylating group via a hydrophilic polyethylene glycol tether.
8. A process according to claim 7, where the tether has an average molecular weight of less than 1000 Daltons.
9. A process according to claim 1, further comprising removing the protecting groups.
10. A process according to claim 3, further comprising removing the protecting groups.
11. A process according to claim 7 where the fatty portion is a oleoyl, palmitoyl, or stearyl group.
12. A process according to claim 7 where the molar ratio of acylating agent to protected LPEI is 1:1 to 40:1.
13. A process according to claim 7, wherein the cross-linking agent is a dithiodipropionyl halide.
14. A process according to claim 7, where the cross-linking agent yields a cross-linker group of the formula: —CO(CH$_2$)$_a$SS(CH$_2$)$_a$CO—, where each a is independently an integer from 1 to 15.
15. A process according to claim 7, where the acylating agent is oleoyltetraethyleneglycolcarbonyl chloride.

* * * * *